(12) United States Patent
McKay

(10) Patent No.: US 8,481,064 B2
(45) Date of Patent: Jul. 9, 2013

(54) METHOD FOR DELIVERING A THERAPEUTIC AGENT COMPRISING INJECTION OF MICROSPHERES

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 156 days.

(21) Appl. No.: 12/715,093

(22) Filed: Mar. 1, 2010

(65) Prior Publication Data

US 2010/0189757 A1 Jul. 29, 2010

Related U.S. Application Data

(62) Division of application No. 11/403,733, filed on Apr. 13, 2006, now Pat. No. 7,741,273.

(51) Int. Cl.
*A61K 39/00* (2006.01)
*A61K 38/18* (2006.01)
*A61K 38/19* (2006.01)
*A61K 38/30* (2006.01)

(52) U.S. Cl.
USPC .......... 424/422; 424/133.1; 514/7.5; 514/7.6; 514/8.2; 514/8.5; 514/8.6; 514/8.8; 514/8.9; 514/9.1; 514/17.1

(58) Field of Classification Search
None
See application file for complete search history.

(56) References Cited

U.S. PATENT DOCUMENTS

| | | | |
|---|---|---|---|
| 5,733,572 A * | 3/1998 | Unger et al. | 424/450 |
| 5,756,127 A | 5/1998 | Grisoni et al. | |
| 6,203,813 B1 | 3/2001 | Gooberman | |
| 6,478,776 B1 | 11/2002 | Rosenman et al. | |
| 6,530,934 B1 | 3/2003 | Jacobsen et al. | |
| 6,673,333 B1 * | 1/2004 | Meade et al. | 424/9.35 |
| 6,735,475 B1 | 5/2004 | Whitehurst et al. | |
| 6,971,998 B2 | 12/2005 | Rosenman et al. | |
| 2003/0039613 A1 * | 2/2003 | Unger et al. | 424/9.51 |
| 2004/0034357 A1 | 2/2004 | Beane et al. | |
| 2004/0064193 A1 | 4/2004 | Evans et al. | |
| 2004/0229878 A1 * | 11/2004 | DiMauro et al. | 514/248 |
| 2005/0025765 A1 * | 2/2005 | DiMauro et al. | 424/145.1 |
| 2005/0074481 A1 | 4/2005 | Brekke et al. | |
| 2005/0152949 A1 | 7/2005 | Hotchkiss et al. | |
| 2005/0177118 A1 | 8/2005 | Hoganson et al. | |
| 2005/0245906 A1 | 11/2005 | Makower et al. | |
| 2005/0249775 A1 | 11/2005 | Falotico et al. | |
| 2006/0046961 A1 | 3/2006 | McKay et al. | |

* cited by examiner

*Primary Examiner* — Elizabeth C Kemmerer
(74) *Attorney, Agent, or Firm* — Sorell Lenna & Schmidt LLP

(57) ABSTRACT

The present invention relates to novel drug depot implant designs for optimal delivery of therapeutic agents to subjects. The invention provides a method for alleviating pain associated with neuromuscular or skeletal injury or inflammation by targeted delivery of one or more therapeutic agents to inhibit the inflammatory response which ultimately causes acute or chronic pain. Controlled and directed delivery can be provided by drug depot implants, comprising therapeutic agents, specifically designed to deliver the therapeutic agent to the desired location by facilitating their implantation, minimizing their migration from the desired tissue location, and without disrupting normal joint and soft tissue movement.

18 Claims, 8 Drawing Sheets

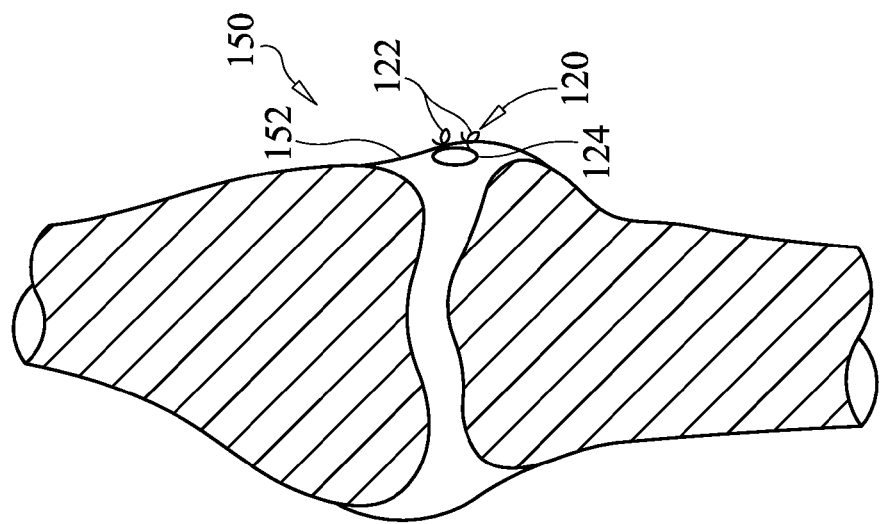
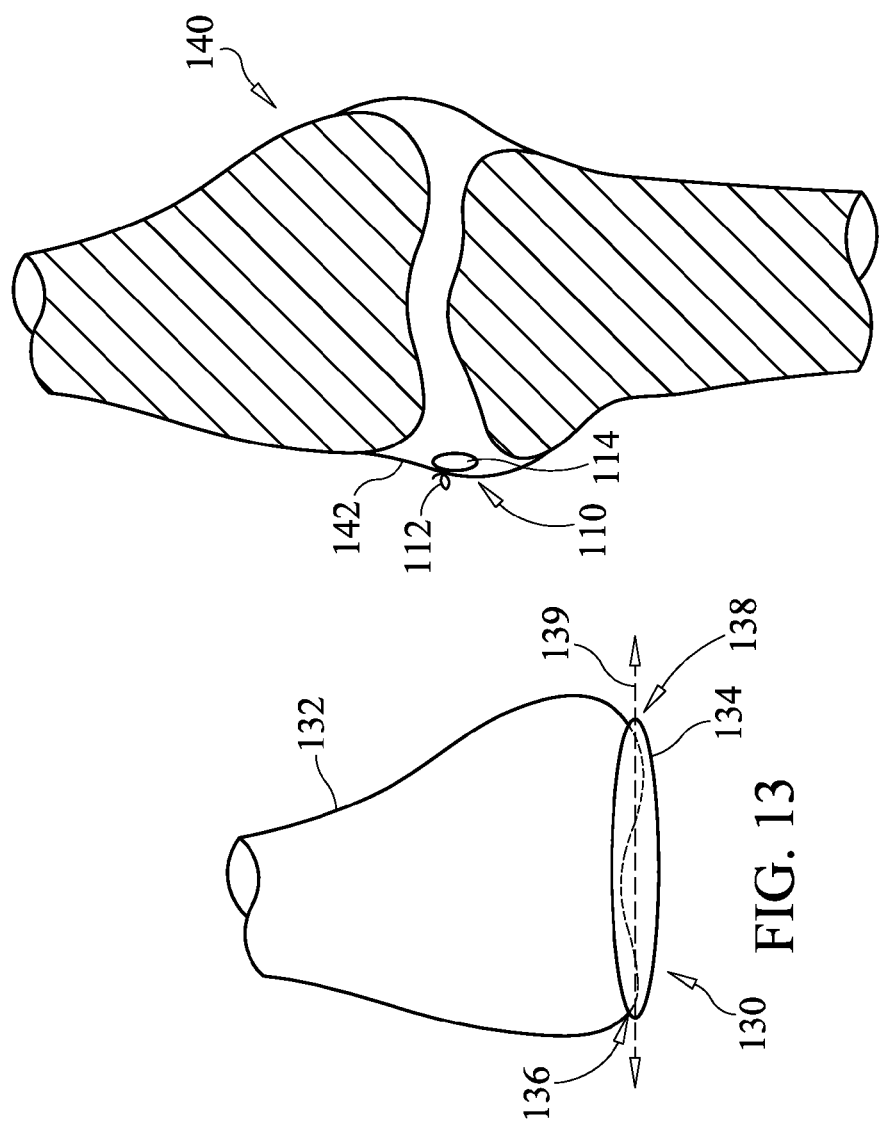

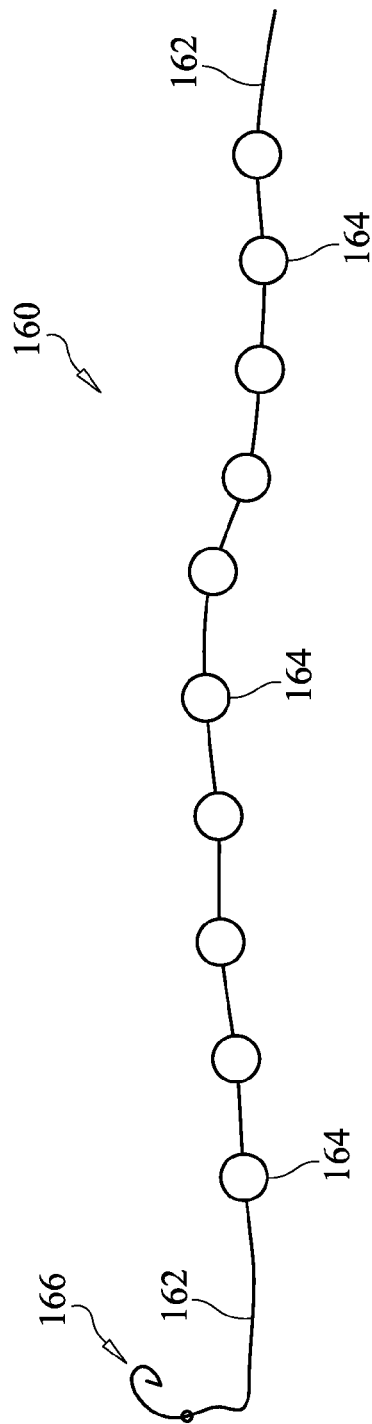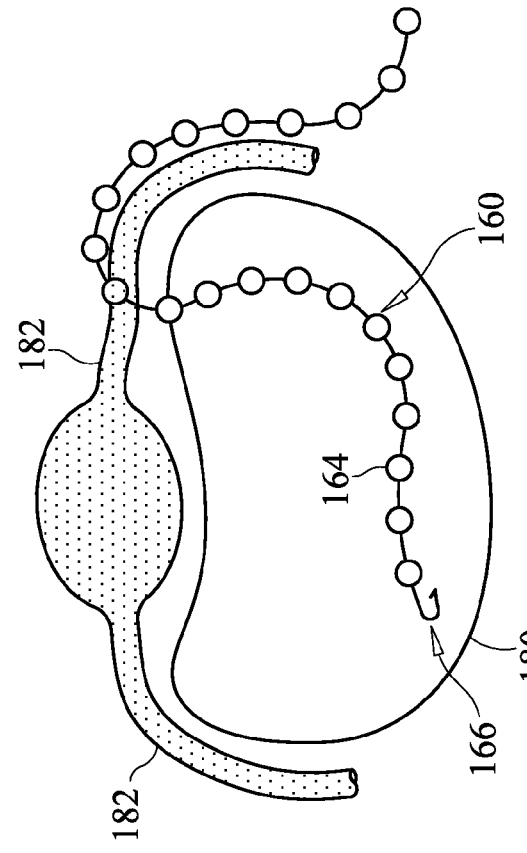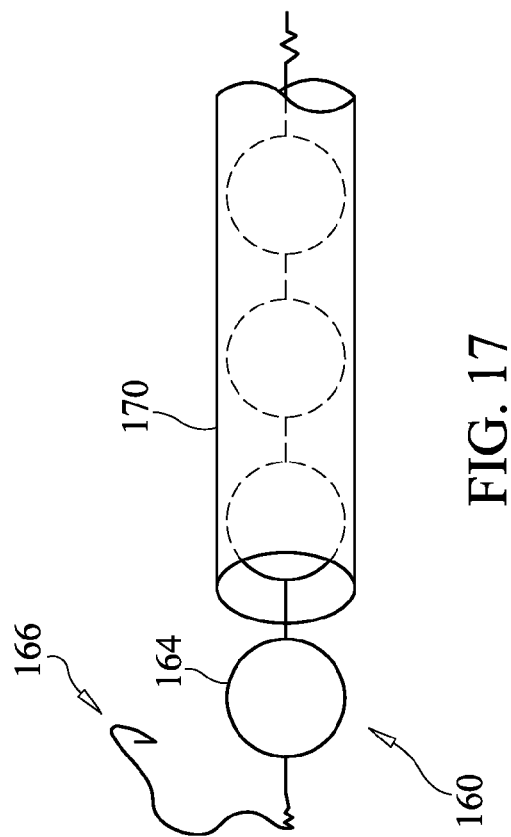

METHOD FOR DELIVERING A THERAPEUTIC AGENT COMPRISING INJECTION OF MICROSPHERES

FIELD OF THE INVENTION

The present invention broadly concerns drug depot implant designs for optimal delivery of therapeutic agents to subjects. In specific applications of the invention the compositions include novel drug depot implant designs for optimal delivery of anti-inflammatory agents and/or growth factors to inhibit or eliminate the inflammatory response that may result in acute or chronic pain and further tissue damage after disease or injury.

BACKGROUND OF THE INVENTION

Current approaches for treating pain and/or inflammation involve systemic delivery of therapeutic agents. Anti-inflammatory agents target tumor necrosis factor alpha (TNF-α) which appears early in the inflammatory cascade following infection or injury. It is produced by monocytes, macrophages, and T lymphocytes. TNF-α exerts its primary effects on monocytes, synovial macrophages, fibroblasts, chondrocytes, and endothelial cells, and stimulates proinflammatory cytokine and chemokine synthesis. It activates granulocytes, and increases MHC Class II expression. It promotes secretion of matrix metalloproteinases (MMPs), leading to cartilage matrix degradation. Because it initiates an inflammatory cascade, and has been found to be increased in close proximity to inflamed or injured tissue, TNF-α inhibition is a target for pain therapy. Pro-TNF-α is expressed on the plasma membrane, then cleaved in the extracellular domain. Trimerization is required for biological activity. TNF-α acts through two receptors (TNFRs): Type I receptors (p60, p55, CD 120a) are expressed constitutively on most cell types and Type II receptors (p80, p75, CD 120b) are inducible. Popular TNF-α inhibitors act primarily to inhibit binding of TNF-α to its receptors. There are currently two major classes of TNF inhibitors: 1) monoclonal antibodies to TNF-α, which prevent binding of TNF-α to its two cell-associated signaling receptors (p55 and p75) and 2) monomeric soluble forms of p55 or p75 TNFR dimerized by linking them to an immunoglobulin (Ig) Fc fragment. These Igs bind to TNF-α with high affinity and prevent it from binding to its cell-associated receptor.

TNF inhibitors have therefore been developed for therapeutic use for orthopedic and neuromuscular disease or injury that can cause pain, such as rheumatoid arthritis. Currently therapeutic agents are delivered systemically to treat bone and cartilage related defects related to degeneration, injury, infection, malignancy or developmental malformation. TNF inhibitors currently in use are generally administered systemically via intravenous infusion and subcutaneous injection, but there are side effects of anti-TNF therapies associated with the higher doses and systemic administration that are common with these therapies. A major disadvantage of these systemic drug delivery systems is that the anti-inflammatories are delivered in buffered solutions that have short half-lives, thereby requiring repeated administration to a patient, which can result in adverse effects due to the system of delivery of relatively high doses of the drug. Unfortunately, it provides a limited quantity of agent that must move through the tissue to the target site. This method is inadequate to serve the needs of patients. Anti-TNF therapy is generally needed over an extended period of time, so repeated injections are likely to be necessary. In addition, injection site pain and reactions sometimes develop with anti-TNF agents.

Recently, there have been a number of attempts to develop an acceptable implant and methods for treating disease in a patient.

U.S. Pat. No. 6,203,813 discloses an opiate antagonist implant pellet for subcutaneous administration to a patient. According to the disclosure, the subcutaneous implant pellet releases the opiate antagonist in the patient to effectively inhibit the effects of a number of additive drugs to treat drug detoxification in a patient. The subcutaneous implant is not substantially immobilized in the tissue of a patient but is free to move about under the skin. Another drawback to this approach is that the delivery of the therapeutic agent is accomplished via the general systemic circulatory system and not it's local effect.

U.S. Pat. No. 6,735,475 discloses small implantable stimulators with at least two electrodes that are small enough to have the electrodes located adjacent to a nerve structure at least partially responsible for headache and/or facial pain. The implant works via electrical stimulation of a specified tissue and does not include a therapeutic agent component as part of the device, let alone involve delivery of a therapeutic agent to desired tissue. U.S. Pat. No. 6,735,475 describes a variety of implants, for treating headache and/or facial pain, none of which are suitable for introducing therapeutic agents to a desired tissue of a patient.

U.S. Patent Application Publication No. 20040064193 discloses an implant comprising collagen and or other bio-resorbable materials for deployment in select locations for regeneration of tissue. According to the disclosure, the implant comprises a synthetic tissue substitute material and a method and system for deploying the implant. U.S. Patent Application Publication No. 20040064193 describes a variety of implants, for regeneration of tissue, none of which are suitable for introducing therapeutic agents to a desired tissue of a patient.

U.S. Patent Application Publication No. 20050074481 discloses an implantable device comprising a polyelectrolytic complex for facilitating the healing of voids in bone, cartilage and soft tissue. According to the disclosure, the implant provides in vivo culturing of tissue cells in a diverse tissue or homogeneous lesion. U.S. Patent Application Publication No. 20050074481 describes a variety of implants, for facilitating the healing of voids in bone, cartilage and soft tissue, none of which are suitable for introducing therapeutic agents to a desired tissue of a patient.

U.S. Patent Application Publication No. 20050177118 also discloses an implantable device comprising a polyelectrolytic complex for facilitating the healing of voids in bone, cartilage and soft tissue. According to the disclosure, the implant provides in vivo culturing of tissue cells in a diverse tissue or homogeneous lesion, or for non-systemic delivery of one or more therapeutic agents to a patient. The implant provides an electrical component as part of the device and does not include a therapeutic agent component as part of the device, let alone involve delivery of a therapeutic agent to desired tissue.

U.S. Patent Application Publication No. 20050152949 discloses a method of intra-articular drug delivery comprising: selecting an attachment zone within the subchondral bone in a synovial joint, affixing a drug release device in the attachment zone, the drug release device comprising a base affixable in the attachment zone, a sustained release drug carrier and a drug, the device positioned so that the device releases the drug into the synovial fluid of the synovial joint, and so that agitation of the synovial fluid facilitates elution of the drug from the drug release device. One drawback of these implants is that they are fixedly attached to the bone itself in a synovial joint. Another drawback of these implants is that many of the intended patients already suffer from pain and inflammation, and will be subjected to more pain upon implantation of the device into the bone and possible formation of osteophytes.

Despite the advances recently made in the art, there is an immediate need for improved medical devices, methods and systems for targeted delivery of therapeutic agents, such as TNF inhibitors, for the treatment and prevention of inflammation and pain, capable of being delivered for an extended period of time at, or in close proximity to, a targeted site such as the site of trauma or inflammation.

SUMMARY OF THE INVENTION

The present invention fills the foregoing need by providing a drug depot implant comprising a physical structure to facilitate implantation and retention in a synovial joint, a disc space, a spinal canal, or a soft tissue surrounding the spinal canal of a subject; and a therapeutic agent that creates a concentration gradient for targeted delivery of the agent to the synovial joint, the disc space, the spinal canal, or the soft tissue surrounding the spinal canal, muscle, tendon, ligament, or cartilage of a subject.

One aspect of the present invention, which provides the use of depots to deliver anti-inflammatory or anabolic compounds to intervertebral discs or articulating joints, has not been previously disclosed. Another aspect of the present invention provides specific designs and methods for insertion of drug depots into discs or joint capsules with minimal tissue disruption and minimal interference with normal joint motion. The methods, systems and reagents of the present invention prevent the depots from migrating away from the inflamed tissue, and allow for more uniform distribution of the drug.

One aspect of the invention provides a method for reducing pain and/or inflammation, which comprises administering to a target site in a subject in need of treatment an effective amount of a pharmaceutical composition comprising one or more therapeutic agents, wherein the one or more therapeutic agents are administered by a drug depot implant. In one embodiment, the drug depot implant comprises a body that holds the therapeutic agent, and an anchoring system that extends from the body to prevent migration of the body from the target site.

One aspect of the present invention provides for a solid depot, wherein the therapeutic agent is in lyophilized form within the implant and slowly releases an effective therapeutic amount of agent into the desired location over a prolonged period of time, such as for example, up to and including six months.

In the practice of the invention, a drug depot implant is implanted in a subject at or near a target site. Non-limiting examples of such sites include an inflamed nerve, a synovial joint, or a spinal site, in particular a spinal disc site, such as the spinal disc space, the spinal canal or the surrounding soft tissue.

In accordance with one aspect of the present invention a drug depot implant design provides a physical feature to facilitate implantation and retention of the implant in the desired anatomical location for optimal clinical efficiency. In one embodiment of the invention the drug depot design is a rod shaped implant loaded with a therapeutic agent. One embodiment of the invention provides a rod shaped implant comprising small barbs that minimize migration of the implant in a patient's tissue once implanted.

The present invention provides for methods, systems and reagents that permit a surgeon to deliver a drug depot implant with optimal efficiency to a target site in a subject in need of treatment. In one embodiment of the invention, the implant is designed to limit "backout" or forward movement into critical tissues. In another embodiment of the invention, the implant is positioned in adjacent soft tissue to the spinal foramen space of inflamed nerve roots to alleviate sciatica and/or back pain caused by such inflammation. An alternative embodiment of the invention provides for a rod depot implant positioned into a disc space, wherein the implant is positioned in place by the barb. In this embodiment of the invention the rod depot may further comprise a built-in cap or "stop" that positions the rod in place by utilizing an adjacent tissue plane, thereby permitting the active end of the rod to protrude into an area of inflamed tissue and elute the therapeutic agent, which may be, for example, an anti-inflammatory agent. In another embodiment of the invention the drug depot implant is positioned in the knee joint, wherein the rod cap is positioned in place by the knee capsule and elutes the therapeutic agent, such as an anti-inflammatory agent, into the knee joint synovial fluid. Additional embodiments of the invention provide for positioning the drug depot implant in the shoulder, hip, other joints or spine of a patient.

In one embodiment, a targeted delivery system of one or more therapeutic agents is conveniently a catheter. In another embodiment, the targeted delivery system is a syringe.

In one method of the invention, the targeted delivery system comprises a drug depot implant system administered locally by insertion of a catheter at or near a target site, the catheter having a proximal end and a distal end, the distal end having an opening to deliver a pharmaceutical in situ, the proximal end being fluidly connected to a pharmaceutical delivery pump. For example, the proximal end of the catheter may deliver the therapeutic agent to within 10 cm of a target site, more particularly, to within 5 cm of the target site.

In the employment of an implant of the invention, the therapeutic agent may inhibit inflammation mediated by TNF-α, for example when the therapeutic agent is a TNF-α receptor inhibitor. Suitable therapeutic agents include, but are not limited to, soluble tumor necrosis factor α receptors, pegylated soluble tumor necrosis factor α receptors, monoclonal antibodies, polyclonal antibodies, antibody fragments, COX-2 inhibitors, metalloprotease inhibitors, such as TAPI, glutamate antagonists, glial cell derived neurotrophic factors (GDNF), B2 receptor antagonists, Substance P receptor (NK1) antagonists, Downstream regulatory element antagonistic modulator (DREAM), iNOS, inhibitors of tetrodotoxin (TTX)-resistant Na+-channel receptor subtypes PN3 and SNS2, inhibitors of interleukins, such as IL-1, IL-6, IL-8 and IL-10, TNF binding protein, dominant-negative TNF variants, Nanobodies™, kinase inhibitors, and combinations thereof. Other suitable therapeutic agents include but are not limited to Adalimumab, Infliximab, Etanercept, Pegsunercept (PEG sTNF-R1), Onercept, Kineret®, sTNF-R1, CDP-870, CDP-571, CNI-1493, RDP58, ISIS104838, 1>3-β-D-glucans, Lenercept, PEG-sTNFRII Fc Mutein, D2E7, Afelimomab, AMG 108, 6-methoxy-2-napthylacetic acid) or betamethasone, capsaicin, civamide, TNFRc, ISIS2302 and GI 129471, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, HuMax IL-15 (anti-IL antibodies) and combinations thereof. Still other therapeutic agents include, but are not limited to, NF Kappa B inhibitors, such as glucocorticoids including clonidine; nonsteroidal anti-inflammatory drugs (NSAIDs), such as salicylates, diflunisal, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac and tepoxalin; antioxidants, such as dithiocarbamate, and other compounds such as sulfasalazine [2-hydroxy-5-[-4-[C2-pyridinylamino)sulfonyl]azo]benzoic acid] and steroids, such as fluocinolone, cortisol, cortisone, hydrocortisone, fludrocortisone, prednisone, prednisolone, methylprednisolone, triamcinolone, betamethasone, dexamethasone, beclomethasone and fluticasone.

In certain embodiments, the therapeutic agent is an osteoinductive factor. Suitable osteoinductive factors include, but are not limited to, a bone morphogenetic protein, a growth differentiation factor or biologically active fragment or variant thereof, a LIM mineralization protein or biologically active fragment or variant thereof, or combinations thereof.

Also disclosed is that the one or more therapeutic agents within the drug depot implant are incorporated into a sustained release pharmaceutical composition. In one embodiment, two or more therapeutic agents are incorporated into a sustained release pharmaceutical composition. For example, in one embodiment two or more therapeutic agents are separately incorporated into separate biocompatible polymers.

The invention also includes a drug depot implant for treating osteolysis and/or bone resorption comprising administering a drug depot implant to an osteolytic site in a subject in need of treatment, the drug depot implant providing an effective amount of a pharmaceutical composition comprising one or more therapeutic agents, wherein administration of the pharmaceutical composition is localized and sustained.

In one embodiment, the one or more therapeutic agents includes at least one osteoinductive factor. Examples of suitable osteoinductive factors include a bone morphogenetic protein, a growth differentiation factor or a biologically active fragment thereof, a LIM mineralization protein or a biologically active fragment thereof, or combinations thereof.

In yet another embodiment, a method is provided for alleviating pain associated with bone tumors, the method comprising administering to a tumor site in a subject in need of treatment a drug depot implant comprising an effective amount of one or more therapeutic agents, wherein administration of the composition is localized and sustained. In this method the one or more therapeutic agents includes at least one osteoinductive factor. Suitable examples include, but are not limited to, a bone morphogenetic protein, a growth differentiation factor or a biologically active fragment or variant thereof, a LIM mineralization protein or a biologically active fragment or variant thereof, or combinations thereof.

Also provided is a system for providing pain relief medication in a mammalian subject, the system comprising a depot for providing controlled and directed delivery of at least one therapeutic agent to a target site in a subject in need thereof comprising an effective amount of a composition comprising at least one therapeutic agent which decreases inflammation at the target site. In another embodiment, the therapeutic agent further comprises a modified release pharmaceutical composition. The system can further comprise two or more therapeutic agents. In still another embodiment, a catheter is provided rather than a depot. In this embodiment, a catheter has a proximal end and a distal end, the distal end having an opening to deliver a pharmaceutical in situ, the proximal end being fluidly connected to a pharmaceutical pump. In another embodiment, the distal end of the catheter delivers the therapeutic agent within about 10 cm of, or closer to, the target site. In another embodiment, the catheter delivers the therapeutic agent within about 5 cm of, or closer to, the target site. In this system, the at least one therapeutic agent may inhibit inflammation mediated by TNF-$\alpha$. Suitable examples of a therapeutic agent is a TNF-$\alpha$ receptor inhibitor, for example, a pegylated soluble TNF-$\alpha$ receptor. Other suitable therapeutic agents are listed herein. The system may further comprise a therapeutically effective amount of at least one osteoinductive factor. Suitable osteoinductive factors include, but are not limited to, a bone morphogenetic protein, a growth differentiation factor or a biologically active fragment or variant thereof, a LIM mineralization protein or a biologically active fragment or variant thereof, or combinations thereof. In one embodiment, the system of the invention employs a depot comprising a modified release pharmaceutical carrier.

The invention also includes the use of a composition comprising one or more therapeutic agents that decrease inflammation at a target site for the manufacture of a pharmaceutical for reducing pain, wherein administration of an effective amount of the composition to a target site in a subject in need of treatment is localized and controlled.

In one embodiment, the invention is a depot for alleviating pain and limiting bone loss associated with osteolysis, wherein the administration of the composition to an osteolytic site in a subject in need of treatment is localized and controlled.

In another embodiment the invention includes the use of a composition comprising one or more therapeutic agents that decrease inflammation at a target site for the manufacture of a pharmaceutical for alleviating pain associated with bone tumors, wherein administration of the composition to a tumor site in a subject in need of treatment is localized and controlled.

In any of the above listed uses, the composition may be a sustained release pharmaceutical composition.

Also disclosed is a method for retarding tissue necrosis and/or damage, the method comprising administering to a target site in a subject in need of treatment an effective amount of a pharmaceutical composition comprising one or more therapeutic agents, wherein the one or more therapeutic agents are administered by a depot that provides localized and sustained release of the pharmaceutical composition. In one embodiment, the depot is implanted in a subject at or near a target site, such as, but not limited to, an inflamed nerve or a spinal site, for example into a spinal disc or spinal disc space.

One aspect of the invention provides a radiographic marker on the drug depot implant to permit a surgeon to accurately position the implant into a tissue of a patient. Examples of such radiographic markers include, but are not limited to, barium, calcium phosphate, and metal beads. Such radiographic markers will also permit the surgeon to track movement and degradation of the implant in the tissue over time. In this embodiment of the invention the surgeon may accurately position the implant in the tissue using any of the numerous diagnostic imaging procedures known to one of ordinary skill in the art. Such diagnostic imaging procedures include, for example, X-ray imaging or fluoroscopy.

Another aspect of the present invention provides for methods, systems and reagents comprising a drug depot implant configuration for providing a concentration gradient of the therapeutic agent to the tissue of a patient. In this aspect of the invention the preferred drug depot implant is a rod configuration that provides an optimal, therapeutically effective amount of the therapeutic agent up to 1 to 5 cm from the rod.

Another aspect of the present invention provides for drug depot implant configurations comprising microspheres loaded with a therapeutic agent, such as a TNF-inhibitor, for targeted delivery to a desired region of a patient. In this embodiment of the invention, targeted drug depot delivery my be achieved by any means including for example, by injection either into the disc space, the spinal canal, or in the surrounding soft tissues. This embodiment of the present invention delivers the therapeutic agent closer to the inflamed tissue e.g., nerve roots causing sciatic pain, nerve fibers growing into annular tears in discs causing backpain, or knee joints with osteoarthritis. It will be appreciated by those with skill in the art that a drug delivery device may be delivered by a wide variety of methods, such as by placement into a drill site, injection by syringe and/or catheter or forceful injection by gun.

These and other objects and advantages of the present invention will be apparent from the descriptions herein.

BRIEF DESCRIPTION OF THE FIGURES

FIG. 13 is a side view of yet another alternative of a drug depot implant.

FIG. 14 shows the drug depot implant of FIG. 11 deployed in a joint.

FIG. 15 shows the drug depot implant of FIG. 12 deployed in a joint.

FIG. 16 is a side view of another drug depot implant.

FIG. 17 shows the drug depot implant of FIG. 16 and an associated targeted delivery system.

FIG. 18 shows the drug depot implant of FIG. 16 deployed in a disc and surrounding soft tissue.

DETAILED DESCRIPTION

Figure 1:
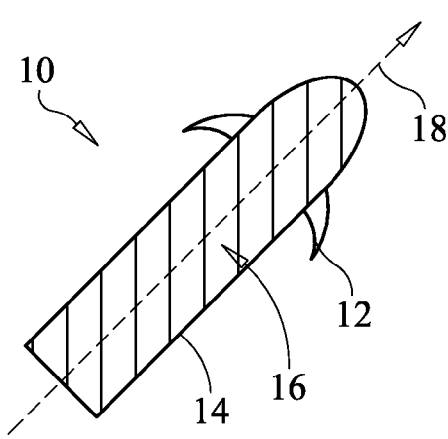
FIG. 1 is a cross-sectional view of one embodiment of a drug depot implant.

For the purposes of promoting an understanding of the principles of the invention, reference will now be made to preferred embodiments and specific language will be used to describe the same. It will nevertheless be understood that no limitation of the scope of the invention is thereby intended, such alterations and further modifications of the invention, and such further applications of the principles of the invention as illustrated herein, being contemplated as would normally occur to one skilled in the art to which the invention relates.

The present invention provides methods, systems and reagents for facilitating implantation of a drug depot implant into a subject comprising implanting an implant depot loaded with a therapeutic agent. The drug depot implants of the present invention may be designed for placement and location within or near the synovial joint, the spinal disc space, the spinal canal or the surrounding soft tissue.

The present invention also provides methods, systems and regents for decreasing, eliminating, or managing pain—especially pain of neuromuscular or skeletal origin—by providing direct and controlled delivery, i.e., targeted delivery of at least one therapeutic agent to one or more sites of inflammation and sources of pain. A therapeutic agent itself may be on a continuum of rapid acting to long acting. Generally, the therapeutic agent is a component of a pharmaceutical composition which can range in a continuum of rapid release to sustained release. Still further, the delivery of that pharmaceutical composition via the targeted delivery system of the invention can include, for example, rapid and repeating delivery at intervals or continuous delivery. The delivery can be "local", "direct" and "controlled."

A drug depot implant of the present invention comprises a physical structure to facilitate implantation and retention in a desired location of a subject, such as for example, a synovial joint, a disc space, a spinal canal, or a tissue of a subject; and a therapeutic agent that provides a concentration gradient for targeted delivery of the therapeutic agent to the location. The implant of the present invention provides an optimal drug concentration gradient of the therapeutic agent at a distance of about 1 cm to about 5 cm from the implant. The implant of the present invention may further comprise an insertion cannula for delivery of the therapeutic agent to the subject. One aspect of the present invention provides a depot attached to a probe, wherein the probe is released by a pull-back mechanism for delivery of the therapeutic agent to the subject. The implant of the present invention may further comprise a barb for minimizing migration of the implant in a tissue of a subject. The implant of the present invention may still further comprise a cap for retaining the depot in a tissue membrane or between tissue planes.

An aspect of the present invention provides an injectable drug depot implant comprising microspheres loaded with a therapeutic agent, wherein the microspheres are injected into a synovial joint, a disc space, a spinal canal, or a soft tissue surrounding the spinal canal.

Another aspect of the present invention provides a drug depot implant comprising a gel in viscous form and microspheres loaded with a therapeutic agent, wherein the combination of gel and microspheres are positioned into a synovial joint, disc space, a spinal canal, or a soft tissue surrounding the spinal canal of a subject. In one embodiment of the present invention, the gel is a sprayable or injectable adherent gel that solidifies upon contact with tissue.

One aspect of the invention provides that the viscous gel loaded with microspheres also delivers the microspheres to the desired inflamed tissue location and prevents the microspheres from being removed from that area by the venous systemic vasculature or otherwise dispersed too widely to get the desired therapeutic effect. In this aspect of the invention, after a few hours or days the gel may be absorbed, thereby allowing the microspheres to begin releasing the therapeutic agent. The microspheres do not begin releasing the agent until they are released from the gel. So, the microspheres must be formed from something that is insoluable or inert in the gel, but soluable or active once it comes into contact with the targeted tissue. The gel must be something that dissolves or disperses within the subject tissue. The purpose of the gel is as you have described. As the gel begins to dissolve within hours-days, the microspheres are exposed to body fluids and begin releasing their contents. Examples of gels could be gelatin, PEG, or POE. Sp the gel could be a different material from the microspheres or the same ie. POE. The gel and microspheres are formulated to optimize exposure time of the micospheres and release of the therapeutic agent from the microspheres.

The present invention provides numerous designs for the drug depot.

One aspect of the invention provides that when depot barbs are employed they can be oriented in one direction to facilitate implantation while also preventing backing out or expulsion of the depot from the desired tissue location. In another aspect of the invention the barbs could also be oriented in opposite directions to prevent movement in either direction once implanted.

Another aspect of the invention provides that the barbs could be fixed protrusions or flexible protrusions that deflect out once implanted.

Another aspect of the invention provides that a joint capsule depot has barbs in combination with a cap such that once the depot is inserted into the wall of the joint capsule the barb deploys and holds the depot in place via the cap and deployed barbs. In this aspect of the invention, the barbs keep the depot from backing out and the cap keeps it from completely going into the joint space. In another aspect of the invention the depot can be designed such that the therapeutic agent is embedded only in the portion of the depot protruding into the joint space synovial fluid. In this aspect of the invention as the joint articulates it facilitates the distribution of the therapeutic agent throughout the synovial fluid. In one embodiment, after 3-6 months the depot completely degrades and so no longer transverses the joint capsule.

In another aspect of the invention, radiopaque marks are positioned in the depot at opposite ends of the depot to assist in determining the position of the depot relative to the inflamed tissue to be treated. In this aspect of the invention the radiopaque marker could be a spherical shape, or a ring around the depot.

The present invention contemplates the use of rod-shaped depots in joint capsules, in which the depots contain one or more sutures for retaining the depot up against the inside of the joint capsule.

The present invention also provides a depot shaped as a tapered rod with a bullet shaped tip to ease insertion of the depot through the joint capsule tissue and minimize tissue disruption. In this aspect of the invention, the depot may contain a suture that is embedded into a biodegradable rod during manufacture of the depot. In one embodiment of the invention, the suture is strategically positioned within the rod to facilitate positioning the depot adjacent to the inside of the joint capsule.

In a further embodiment, a very small hole is made in the joint capsule with a blunt probe, then the tapered rod is slowly pushed through this hole, slowly stretching the tissues apart to minimize tissue tearing. Once the rod is fully inserted, the hole in the joint capsule closes upon itself. The suture embedded in the rod is left transversing through the capsule so that it can be pulled taught and knotted up against the outside of the joint capsule, forcing the depot up against the inside of the joint capsule. Having the depot up against the inside of the joint capsule will prevent the depot from interfering with normal joint motion.

In various embodiments, the suture can exit through the ends of the rod, in the middle, or somewhere in-between. The suture can exit through just one hole through the joint capsule or through two or more holes. In a preferred design, the suture exits the rod at two points near the ends of the rod and passes through two points in the joint capsule. This design offers the advantage of holding the depot up against the inside of the joint capsule without rotating and potentially interfering with joint motion.

Another aspect of the present invention provides several designs that are contemplated for use in the intervetebral disc and joint capsules, which includes bead shaped depots strung together along a suture. In this aspect of the invention, the beads may be a drug loaded biodegradable polymer, and the suture may be either degradable or non-degradable material. One embodiment of the invention provides at the leading end of the suture an optional needle or barb to retain the strand within the disc or joint capsule.

Another aspect of the invention provides that the strand may be implanted by inserting a cannula, which contains the strand of beads, inside the disc, joint, or soft tissue as far as desired, then deploying the barb into the soft tissue (e.g., the annulus) and slowly retracting the cannula, which will result in the string of beads being pulled from the cannula. One embodiment of the invention provides that by fixing the leading edge of the string of beads, the beads are retained at the location where the drug is desired inside a disc, along a nerve root, or transverse across a joint, resulting in a more uniform distribution of the drug.

In one embodiment, the string of drug eluting bead depots are disposed along the route of inflamed tissue, thereby resulting in a more effective distribution of the drug and greater clinical effectiveness. For example, a very small hole may be made in an intervertebral disc at the site of a possible disc herniation or in a joint capsule with a blunt probe through which a cannula may be inserted to implant the string of beads.

Another aspect of the present invention provides a method for delivering a therapeutic agent to a synovial joint, disc space, a spinal canal, or a soft tissue surrounding the spinal canal of a subject, comprising inserting within the synovial joint, the disc space, the spinal canal, or the soft tissue surrounding the spinal canal of a subject, a drug depot implant comprising a hollow depot, the hollow depot comprising a therapeutic agent that provides a concentration gradient for targeted delivery of the agent to the synovial joint, the disc space, the spinal canal, or the soft tissue surrounding the spinal canal of a subject. One embodiment of the invention provides for an optimal drug concentration gradient extending about 1 to about 5 cm from the implant. Another embodiment of the present invention provides for delivering the therapeutic agent to the synovial joint or tissue using an insertion cannula.

Another embodiment of the present invention provides for the drug depot implant further comprising a barb for minimizing migration of the implant in a tissue of a subject, and further comprising a cap for retaining the depot in a tissue membrane or between tissue planes.

Another aspect of the present invention provides a method for delivering a therapeutic agent to a synovial joint, disc space, a spinal canal, or a soft tissue surrounding the spinal canal of a subject, comprising inserting within the synovial joint, the disc space, the spinal canal, or the soft tissue surrounding the spinal canal of a subject a drug depot implant comprising microspheres, the microspheres comprising a therapeutic agent that provides a concentration gradient for targeted delivery of the agent to the subject, wherein the microspheres are injected into the synovial joint, the disc space, the spinal canal, or the soft tissue surrounding the spinal canal.

Another aspect of the present invention provides a method for delivering a therapeutic agent to a synovial joint, a disc space, a spinal canal, or a soft tissue surrounding the spinal canal of a subject, the method comprising inserting within the synovial joint, the disc space, the spinal canal, or the soft tissue surrounding the spinal canal of a subject a drug depot implant comprising a gel in viscous form and microspheres loaded with a therapeutic agent. The combination of gel and microspheres are positioned into the synovial joint, the disc space, the spinal canal, or the soft tissue surrounding the spinal canal of a subject. In one embodiment of the present invention, the gel is a sprayable or injectable adherent gel that hardens upon contact with tissue.

To aid in the understanding of the invention, the following non-limiting definitions are provided:

The terms "comprise," "comprising," "include," "including," "have," and "having" are used in the inclusive, open sense, meaning that additional elements may be included. The terms "such as", "e.g.", and "i.e." as used herein are non-limiting and are for illustrative purposes only. "Including" and "including but not limited to" are used interchangeably.

As used herein, the term "anabolic compound" is an art-recognized term and referres to any compound that is involved in the synthesis of more complex substances from simpler ones in living tissue.

As used herein, the term "drug delivery device" is an art-recognized term and refers to any medical device suitable for the application of a drug to a targeted organ or anatomic region. The term includes those devices that transport or accomplish the instillation of the compositions towards the targeted organ or anatomic area, even if the device itself is not formulated to include the composition. As an example, a needle or a catheter through which the composition is inserted into an anatomic area or into a blood vessel or other structure related to the anatomic area is understood to be a drug delivery device. As a further example, a stent or a shunt or a catheter that has the composition included in its substance or coated on its surface is understood to be a drug delivery device. A drug delivery device can include a rigid or flexible container. It may include a semi-solid composition that releases the drug by dissolution of the device or by leaching of drug from the device. It should also be clear that "implant" covers attaching to the joint in any way, e.g., by implanting into a cavity in bone or cartilage or by suturing or otherwise adhering the device to the surface of bone, tendon, or cartilage.

As used herein, the term "microspheres" shall mean generally spherical particles 10 μm-100 μm in size. Microspheres comprise a hollow space encapsulated by lipids, polymers, at least one surfactant, or any combination thereof, wherein the hollow space comprises a therapeutic agent. In different embodiments, microspheres may include microbubbles and liposomes.

As used herein, the term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

As used herein, the term "patient," "subject," or "host" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

As used herein, the term a "targeted delivery system" is a direct and local administration system to deliver therapeutic agents and includes, but is not limited to, a depot, or a system administered locally by insertion of an implant, catheter or syringe at or near a target site. In some embodiments of the invention, the catheter or syringe is optionally operably connected to a pharmaceutical delivery pump. It is understood that pumps can be internal or external as appropriate. A "depot" includes, but is not limited to, capsules, microspheres, particles, gels in viscous forms, coatings, matrices, wafers, pills or other pharmaceutical delivery compositions. A depot may comprise a biopolymer that is either biodegradable or non-degradable.

A "therapeutically effective amount" is such that when administered, the agent results in alteration of the biological activity, such as, for example, inhibition of inflammation. The dosage administered, as single or multiple doses, to an individual will vary depending upon a variety of factors, including the agent's pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art, as well as in vitro and in vivo methods of determining the alteration of biological activity in an individual, such as the inhibition of TNF or IL-1. According to the invention, the therapeutic agent is used in an amount typically ranging between about 0.1 to 5000 μg/kg of body weight or about 1 to 1000 μg/kg of body weight. Amounts of about 10 to 500 μg/kg of body weight are preferred, and amounts of about 50 to 250 μg/kg of body weight are further preferred.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

"Localized" delivery is defined herein as non-systemic delivery wherein one or more therapeutic agents are deposited within a tissue, for example, a nerve root of the nervous system or a region of the brain, or in close proximity (within about 10 cm, or preferably within about 5 cm, for example) thereto. "Targeted delivery system" provides delivery of one or more therapeutic agents in a quantity of pharmaceutical composition that can be deposited at the target site as needed for pain either continuously or at an intermittent rate.

As used herein, the term "therapeutic agents" refers to pharmacologically active substances, such as those that are direct and local-acting modulators of pro-inflammatory cytokines such as TNF-α and IL-1 including but not limited to, for example, soluble tumor necrosis factor α receptors, any pegylated soluble tumor necrosis factor α receptor, monoclonal or polyclonal antibodies or antibody fragments or combinations thereof. Examples of suitable therapeutic agents include receptor antagonists, molecules that compete with the receptor for binding to the target molecule, antisense polynucleotides, and inhibitors of transcription of the DNA encoding the target protein. Suitable examples include but are not limited to Adalimumab, Infliximab, Etanercept, Pegsunercept (PEG sTNF-R1), sTNF-R1, CDP-870, CDP-571, CNI-1493, RDP58, ISIS 104838, 1>3-β-D-glucans, Lenercept, PEG-sTNFRII Fc Mutein, D2E7, Afelimomab, and combinations thereof. They can decrease pain through their actions as inhibitors or agonists of the release of pro-inflammatory molecules. For example, these substances can act by inhibiting or antagonizing expression or binding of cytokines or other molecules that act in the early inflammatory cascade, often resulting in the downstream release of prostaglandins and leukotrienes. These substances can also act, for example, by blocking or antagonizing the binding of excitatory molecules to nociceptive receptors in the nervous system or neuromuscular system, as these receptors often trigger an inflammatory response to inflammation or injury of the nerve or surrounding tissue through a nitric oxide-mediated mechanism. These therapeutic agents include, for example, inhibitors of the action of tumor necrosis factor alpha (TNF-α). Studies have demonstrated that in chronic arthritic diseases, for example, cartilage degradation continues even when the inflammation has been suppressed. Therapeutic agents such as anti-TNF agents are particularly effective for joint pain, for example, because they not only decrease the inflammation that provides the source of pain but also slow the progression of joint destruction that may accompany the inflammatory response. Hence, local targeted delivery of the therapeutic agents in accordance with the invention may reduce tissue necrosis and damage.

Inflammation can be an acute response to trauma or a chronic response to the presence of inflammatory agents. When tissues are damaged, TNF-α attaches to cells to cause them to release other cytokines that cause inflammation. The purpose of the inflammatory cascade is to promote healing of the damaged tissue, but once the tissue is healed the inflammatory process does not necessarily end. Left unchecked, this can lead to degradation of surrounding tissues and associated chronic pain. Thus, pain can become a disease state in itself. That is, when this pathway is activated, inflammation and pain ensue. Often a vicious and seemingly endless cycle of insult, inflammation, and pain sets in. Examples of conditions in which this cycle is present include, but are not limited to, rheumatoid arthritis, osteoarthritis, carpal tunnel syndrome, lower back pain, lower extremity pain, upper extremity pain, tissue pain and pain associated with injury or repair of cervical, thoracic and/or lumbar vertebrae or intervertebral discs, rotator cuff, articular joint, TMJ, tendons, ligaments and muscles.

It is understood that TNF is both affected by upstream events which modulate its production and, in turn, affects downstream events. Alternative approaches to treating medical conditions exploit this known fact, and therapeutic agents are designed to specifically target TNF as well as molecules upstream, downstream and/or a combination thereof. Such approaches include, but are not limited to modulating TNF directly, modulating kinases, inhibiting cell-signaling, manipulating second messenger systems, modulating kinase activation signals, modulating a cluster designator on an inflammatory cell, modulating other receptors on inflammatory cells, blocking transcription or translation of TNF or other targets in pathway, modulating TNF-α post-translational effects, employing gene silencing, and modulating interleukins, for example IL-1, IL-6 and IL-8. As used herein, "modulating" ranges from initiating to shutting down, and within that range is included enhancing significantly or slightly to inhibiting significantly or slightly. The term "inhibiting" includes a downregulation which may reduce or eliminate the targeted function, such as the production of a protein or the translation of an oligonucleotide sequence. For example, a given patient's condition may require only inhibition of a single molecule, such as TNF, or modulating more than one molecule in a cascade of upstream and/or downstream events in the pathway.

In certain embodiments, TNF-α inhibitors reduce chronic discogenic back and leg pain if delivered by perispinal administration.

In other embodiments, a therapeutic agent is a COX2 inhibitor. Cyclooxygenase inhibitors are a class of enzymes that are believed to regulate the synthesis of prostaglandin E2 (PGE2). PGE2 may increase discogenic back pain by inducing radioculopathy. Inhibiting COX enzymes serves to reduce low back pain. While not intending to be bound to a single theory, it is believed that since they are regulators of PGE2s, they reduce low back pain by decreasing PGE2 production. One suitable COX2 inhibitor (6-methoxy-2-napthylacetic acid) has been shown to suppress PGE2 production and local inflammation in cell culture, as described by Melarange et al. (1992a), "Anti-inflammatory and gastroinstestinal effects of nabumetone or its active metabolite, 6MNA (6-methoxy-2-na[hthylacetic acid): comparison with indomethacin," *Agents Actions*., Spec No: C82-3; and Melarange et al. (1992b) "Anti-inflammatory and gastrointestinal effects of nabumetone or its active metabolite, 6-methoxy-2-naphthylacetic acid (6MNA): Comparative studies with indomethacin," *Dig. Dis. Sci.*, 37(12):1847-1852. Another PGE2 inhibitor includes betamethasone.

Another suitable therapeutic agent is a metalloprotease inhibitor. For example, TAPI is a metalloprotease inhibitor which can block cleavage of TNF-α which, in turn, will reduce production of TNF-α.

Still other suitable therapeutic agents include: glutamate antagonists, glial cell-derived neurotropic factors (GDNF), B2 receptor antagonists, Substance P receptor (NK1) antagonists such as capsaicin and civamide, Downstream regulatory element antagonistic modulator (DREAM), iNOS, inhibitors of tetrodotoxin (TTX)-resistant Na+-channel receptor subtypes PN3 and SNS2, inhibitors of interleukins such as IL-1, IL-6 and IL-8, and anti-inflammatory cytokines such as IL-10.

In one example of an alternative approach, the therapeutic agent is a TNF binding protein. One suitable such therapeutic agent is currently referred to as Onercept. Formulae including Onercept, Onercept-like agents, and derivatives are all considered acceptable. Still other suitable therapeutic agents include dominant-negative TNF variants. A suitable dominant-negative TNF variant includes but is not limited to DN-TNF and including those described by Steed et al. (2003), "Inactivation of TNF signaling by rationally designed dominant-negative TNF variants," *Science*, 301(5641):1895-1898. Still more embodiments include the use of a recombinant adeno-associated viral (rAAV) vector technology platform to deliver oligonucleotides encoding inhibitors, enhancers, potentiators, neutralizers, or other modifiers. For example, in one embodiment an (rAAV) vector technology platform is used to deliver a DNA sequence that is a potent inhibitor of tumor necrosis factor (TNF-alpha). One suitable inhibitor is TNFR:Fc. Other therapeutic agents include antibodies, including but not limited to naturally occurring or synthetic, double chain, single chained, or fragments thereof. For example, suitable therapeutic agents include molecules that are based on single chain antibodies called Nanobodies™ (Ablynx, Ghent Belgium), which are defined as the smallest functional fragment of a naturally-occurring single domain antibody.

Alternatively, therapeutic agents that inhibit kinases and/or inhibit cell signaling are employed. Therapies that fall in this category are capable of manipulating the second messenger systems. Kinase activation signals multiple downstream effectors, including those involving phosphatidylinositol 3-kinase and mitogen-activated protein kinases (MAPK), p38 MAPK, Src and protein tyrosine kinase (PTK). One example includes the signaling of TNFα effects is the downstream activation of MAPK.

Examples of kinase inhibitors are Gleevec, Herceptin, Iressa, imatinib (STI571), herbimycin A, tyrphostin 47, erbstatin, genistein, staurosporine, PD98059, SB203580, CNI-1493, VX-50/702 (Vertex/Kissei), SB203580, BIRB 796 (Boehringer Ingelheim), Glaxo P38 MAP Kinase inhibitor, RWJ67657 (J&J), UO126, Gd, SCIO-469 (Scios), RO3201195 (Roche), Semipimod (Cytokine PharmaSciences) or derivatives of the above mentioned agents. Yet another embodiment of the invention provides for the use of therapeutic agents which block the transcription or translation of TNF-α or other proteins in the inflammation cascade in acute pain.

Therapeutic agents which inhibit TNF-α-post translational effects are useful in the invention. For example, the initiation of TNF-α signaling cascade results in the enhanced production of numerous factors that subsequently act in a paracrine and autocrine fashion to elicit further production of TNF-α as well as other pro-inflammatory agents (IL-1, IL-6, IL-8, HMG-B1). Extracellular TNF-α modifying therapeutic agents that act on the signals downstream of TNF-α are useful in treating systemic inflammatory diseases. Some of these therapeutic agents are designed to block other effector molecules while others block the cellular interaction needed to further induce their production, for example, integrins and cell adhesion molecules.

Suitable therapeutic agents include: integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, and HuMax IL-15 (anti-IL 15 antiboies).

Other suitable therapeutic agents include IL-1 inhibitors. Interleukin-1 is a pro-inflammatory cytokine similar in action to TNF-α. For example, certain inhibitors of this protein are similar to those developed to inhibit TNF-α. One such example is Kineret® (anakinra) which is a recombinant, non-glycosylated form of the human inerleukin-1 receptor antagonist (IL-1Ra). Another suitable therapeutic agent is AMG 108, which is a monoclonal antibody that blocks the action of IL-1.

As mentioned above, pain can become a disease state in itself. One particular area in which this is particularly true is in the lower back and legs. For example, disk herniation is a major cause of back pain and sciatica. Sciatica, or radiculopathy, is pain that radiates down the back of the legs and is generally thought to be caused by irritation of the roots of the sciatic nerve. Back pain can also be caused by spinal stenosis, characterized by overgrowth of bony or soft tissue in the spinal canal with associated pressure on the adjacent nerves. Degeneration of the facet joints between the vertebrae, tumors, infections, fractures, and inflammation of surrounding soft tissues can also cause back pain.

Forces that damage the vertebrae can injure the spinal cord through stretching, laceration, ischemia, or compression. Cancer can metastasize to the spine, resulting in bone destruction and spinal cord compression. Prolonged, continuous pressure on an extremity can result in a crush injury. Prior spine surgery, accompanied by the presence of spinal hardware, makes the spine stiff and vulnerable to additional injury. In all these situations, there is an inflammatory response to the injury. This response can become the source of significant, and often chronic, pain. It is this response that the present invention can address by providing at least one inhibitor of an activator of the response. The inhibitor or combination of inhibitors is provided at, or in close proximity to, the source of inflammation, and is provided in a sustained dosage that is readily available for delivery at regular intervals, continuously, or as needed to manage the inflammatory response. This dosage can be provided, for example, by means of a controlled administration system.

Excitatory amino acids such as glutamate and aspartate have been shown to play a role in the development of pain originating from nerves. Mice with blocked glutamate receptors, for example, have been shown to have a reduction in their responses to pain. Glutamate binds to two major classes of receptors: inotropic glutamate receptors (ligand-gated ion channels) and metabotropic receptors (G protein-coupled receptors). The inotropic receptors in the spinal cord include the N-methyl-D-aspartic acid (NMDA) receptors, the α-amino-3-hydroxy-5-methyl-4-isoxazolepropionate (AMPA) receptors, and the kainite receptors. In the method of the present invention, one or more therapeutic agents can include, for example, antagonists or inhibitors of glutamate binding to NMDA receptors, AMPA receptors, and/or kainate receptors.

Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), for example, may also be useful as therapeutic agents for reducing inflammation. It is contemplated that where desirable a pegylated form of the above may be used.

Examples of other therapeutic agents include NF kappa B inhibitors such as glucocorticoids, including clonidine; antioxidants, such as dilhiocarbamate, and other compounds, such as sulfasalazine[2-hydroxy-5-[-4-[c2-pyridinylamino] sulfonyl]azolbenzoic acid].

Further examples of suitable therapeutic agents include NSAIDs, such as tepoxalin, salicylates, diflunisal, indomethacin, sulindac, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone and gold; other examples include steroids, such as cortisol, cortisone, hydrocortisone, fludrocortisone, prednisone, prednisolone, methylprednisolone, triamcinolone, betamethasone, dexamethasone, beclomethasone and fluticasone.

The invention may further provide an implant comprising a pharmaceutical composition comprising one or more biopolymers and at least one therapeutic agent. Example biopolymers include, but are not limited to, poly(alpha-hydroxy acids), poly(lactide-co-glycolide) (PLGA), polylactide (PLA), polyglycolide (PG), polyethylene glycol (PEG) conjugates of poly(alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, polyphosphoesters, polyanhydrides, polyester-anhydrides, polyamino acids, polyurethane-esters, polyphosphazines, polycaprolactones, polytrimethylene carbonates, polydioxanones, polyamide-esters, polyketals, polyacetals, glycosaminoglycans, hyaluronic acid, hyaluronic acid esters, polyethylene-vinyl acetates, silicones, polyurethanes, polypropylene fumarates, polydesaminotyrosine carbonates, polydesaminotyrosine arylates, polydesaminotyrosine ester carbonates, polydesamnotyrosine ester arylates, polyethylene oxides, polyorthocarbonates, polycarbonates, or copolymers or physical blends thereof or combinations thereof. The biopolymer may also provide for non-immediate (i.e., sustained) release. Examples of suitable sustained release biopolymers include, but are not limited to, poly(alpha-hydroxy acids), poly(lactide-co-glycolide) (PLGA), polylactide (PLA), polyglycolide (PG), polyethylene glycol (PEG) conjugates of poly(alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, or combinations thereof.

The present invention also comtemplates that a gel may be utilized with the drug depot implant, provided that the gel has a consistency sufficient to hold the therapeutic agent i.e., be in a viscous form.

The therapeutic agent, such as for example BMP, may be provided in freeze-dried form and reconstituted in collagen gel, or any other suitable gel carrier. Any suitable gel carrier capable of delivering the therapeutic agent to the target is contemplated.

In certain embodiments, the dosage is provided by means of a drug depot implant, implanted to provide the dosage at, or in close proximity to, the target site.

The ability to deliver pharmaceutical compositions comprising therapeutic agents in effective amounts directly to the site of trauma and/or inflammation is problematic in certain respects. As used herein, a pharmaceutical composition comprises at least one therapeutic agent, as part of a drug depot implant and optionally diluents, excipients and other pharmaceutically acceptable agents desirable for improved stability, manufacturing, efficacy and the like.

It is desirable that the targeted delivery system be able to accurately, precisely and reliably deliver the intended amount of drug over the intended period of time. Many therapeutic agents are quite expensive, especially those formulated to retain stability and efficacy over extended periods of time. Thus, the ability to efficiently formulate, process, package and deliver the therapeutic agent delivered via the targeted delivery system with minimal loss of drug stability and efficacy is desirable. It is desirable that the pharmaceutical compositions suitable for targeted delivery systems of the instant invention be carefully formulated for the desired medical effect in a controlled, local and direct manner. Among the features of the invention is the flexibility of the dosing option made possible due to the unique combinations of the controlled administration system(s) and the pharmaceutical compositions. The drug itself may be on a continuum of rapid acting to long acting. Further, the pharmaceutical composition itself can range in a continuum of rapid release or sustained release. Still further, the options for delivery of that pharmaceutical composition is on a continuum and includes but is not limited to rapid and repeating delivery at intervals ranging to continuous delivery. Delivery may occur at a desired site over a desired period of time for adequate distribution and absorption in the patient. Advantageously, when the targeted delivery system is implanted, the delivery is capable of being directed to sites which are deep, complicated, painful or dangerous to reach by conventional means and/or otherwise inaccessible. As used throughout, the term "a" is intended to include the singular as well as plural.

In one embodiment, the invention provides localized delivery in a controlled manner, such as that provided by the targeted delivery system of the invention. In such an embodiment, the continued up and down cycling of therapeutic agent levels in the patient can be avoided, allowing the body to adjust more easily to the level of the therapeutic agent. Side effects can therefore be minimized.

The targeted delivery system of the invention may additionally include, for example, an infusion pump that administers a pharmaceutical composition through a catheter near the spine or one or more inflamed joints, an implantable mini-pump that can be inserted at an inflammatory site or site of injury or surgery, an implantable controlled release device (such as, for example, the device described in U.S. Pat. No. 6,001,386), and a sustained release delivery system (such as the system described in U.S. Pat. No. 6,007,843).

The pharmaceutical composition can also be administered in a controlled and sustained manner by implanting the desired one or more therapeutic agents dispersed within a depot such as polymer matrix that breaks down over time within the tissues, or otherwise incorporated within a protective coating that provides for the delay of the release of the one or more therapeutic agents.

One example of a suitable pump is the SynchroMed® (Medtronic, Minneapolis, Minn.) pump. This pump has three sealed chambers. One contains an electronic module and battery. The second contains a peristaltic pump and drug reservoir. The third contains an inert gas, which provides the pressure needed to force the pharmaceutical composition into the peristaltic pump. To fill the pump, the pharmaceutical composition is injected through the reservoir fill port to the expandable reservoir. The inert gas creates pressure on the reservoir, and the pressure forces the pharmaceutical composition through a filter and into the pump chamber. The pharmaceutical composition is then pumped out of the device from the pump chamber and into the catheter, which will direct it for deposit at the target site. The rate of delivery of pharmaceutical composition is controlled by a microprocessor. This allows the pump to be used to deliver similar or different amounts of pharmaceutical composition continuously, at specific times, or at set intervals between deliveries.

Potential drug delivery devices suitable for adaptation for the method of the invention include but are not limited to those described, for example, in U.S. Pat. No. 6,551,290 (Elsberry, et al.), which describes a medical catheter for target specific drug delivery; U.S. Pat. No. 6,571,125 (Thompson), which describes an implantable medical device for controllably releasing a biologically-active agent; U.S. Pat. No.

6,594,880 (Elsberry), which describes an intraparenchymal infusion catheter system for delivering therapeutic agents to selected sites in an organism; and U.S. Pat. No. 5,752,930 (Rise, et al.), which describes an implantable catheter for infusing equal volumes of agents to spaced sites.

Additional designs which may be adapted to be employed in the method of the present invention are provided, for example, in U.S. patent applications such as US 2002/0082583 (a pre-programmable implantable apparatus with a feedback regulated delivery method), US 2004/0106914 (a micro-reservoir osmotic release system for controlled release of chemicals), US 2004/0064088 (a small, light-weight device for delivering liquid medication), US 2004/0082908 (an implantable microminiature infusion device), US 2004/0098113 (an implantable ceramic valve pump assembly), and US 2004/0065615 (an implantable infusion pump with a collapsible fluid chamber). Alzet® osmotic pumps (Durect Corporation, Cupertino, Calif.) are also available in a variety of sizes, pumping rates and durations suitable for use in the method of the present invention.

The polymers of the present invention may be employed in the preparation of extended-release or sustained release compositions for use in the method of the present invention. In one embodiment, further excipients are employed. The amount of excipient that is useful in the composition of this invention is an amount that serves to uniformly distribute the active agent throughout the composition so that it can be uniformly dispersed when it is to be delivered to a subject in need thereof. It may serve to dilute the therapeutic agent to a concentration at which the therapeutic agent can provide the desired beneficial palliative or curative results while at the same time minimizing any adverse side effects that might occur from too high a concentration. It may also have a preservative effect. Thus, for a therapeutic agent that has high physiological activity, more of the excipient will be employed. On the other hand, for a therapeutic agent that exhibits a lower physiological activity a lesser quantity of the excipient will be employed. In general, the amount of excipient in the composition will be between about 50% weight (w) and 99.9% w. of the total composition. For therapeutic agent that have a particularly high physiological activity, the amount will be between about 98.0% and about 99.9% w.

Delivery of therapeutic agents to decrease or eliminate pain in a human or animal subject by the method and systems of the present invention can be effective for alleviating pain, although amounts of any one or more therapeutic agents administered to a particular subject are at least one order of magnitude less than those amounts of therapeutic agents, such as TNF-α inhibitors or antagonists, that are provided to individuals who undergo systemic infusion or injection. By providing one or more therapeutic agents at or in close proximity to the site of inflammation or nerve damage, particularly when those therapeutic agents are provided in a controlled-release manner, the amount of therapeutic agents that must be administered in relation to conventional modes of administration, such as oral or by injection, is decreased. This increases the pharmaceutical efficiency of the therapeutic agent, because it is being directed to the tissue in which its action will provide the greatest effect, such as a nerve root or region of the brain. While systemic delivery or delivery by intravenous injection may provide a sufficient level of therapeutic agent to produce the desired result, it also results in an increased risk of unwanted side-effects, such as risk of infection when anti-TNF-α compositions are repeatedly administered, thus resulting in increases in cost, inconvenience and discomfort to the patient.

Effective dosages for use in the method of the present invention can be determined by those of skill in the art, particularly when effective systemic dosages are known for a particular therapeutic agent. Dosages may typically be decreased by at least 90% of the usual systemic dose if the therapeutic agent is provided as in the method and systems of the present invention. In other embodiments, the dosage is at least 75%, at least 80% or at least 85% of the usual systemic dose for a given condition and patient population. Dosage is usually calculated to deliver a minimum amount of one or more therapeutic agents per day, although daily administration is not required. If more than one pharmaceutical composition is administered, the interaction between the same is considered and the dosages calculated. Intrathecal dosage, for example, can comprise approximately ten percent of the standard oral dosage. Alternatively, an intrathecal dosage is in the range of about 10% to about 25% of the standard oral dosage.

The targeted delivery system of the invention can be positioned to deliver at the site of injury which is causing or will cause inflammation, such as a surgical site, or within about 0.5 to about 10 cm, or preferably less than 5 cm, for example, of the injury or inflammatory site. This site can comprise one or multiple sites in the spine, such as between the cervical, thoracic, or lumbar vertebrae, or can comprise one or multiple sites located within the immediate area of inflamed or injured joints, such as the shoulder, hip, or other joints. Implantation of the drug depot implant can occur simultaneously with surgery to repair a fracture, remove a tumor, etc., or can be performed in individuals who experience pain, especially chronic pain, as the result of earlier trauma, injury, surgery, or other initiation of inflammation.

In one embodiment, a targeted delivery system comprises an interbody pump and a catheter, the catheter having a proximal end and a distal end, the distal end having an opening to deliver a pharmaceutical composition in situ and a proximal end of the catheter being fluidly connected to the interbody pump.

Timing of doses can also be determined by a physician or other appropriate health care professional, or the patient, based upon the condition, for example, severity and duration of pain. Duration of administration of therapeutic agents, interval between doses, size of dose, continuity or spontaneity of dosage administration, are all appropriately determined by an individual's physician. In deciding the timing of doses the health care professional has options such as administering to a target site in a patient an effective amount of a pharmaceutical composition comprising one or more therapeutic agents, wherein the one or more therapeutic agents are administered by a targeted delivery system. The administration can (1) be localized and sustained, (2) occur over a period of at least one day to about 6 months, (3) be continuous or periodic. Further, the health care provider has the choice of selecting a pharmaceutical composition having a targeted release rate. For example, a targeted release rate is from about 24 hours to about 62 days. The health care provider may vary the combinations as the patient provides feedback over the treatment course. Accordingly, the health care provider has numerous options not previously available, especially in the treatment of pain, particularly chronic pain.

The methods, systems and reagents of the present invention may have both human medical and veterinary use, being suitable for use in human children and adults, as well as in other mammals. Implantable controlled-delivery devices or compositions containing therapeutic agents as described herein can be placed during orthopedic surgery to minimize inflammation and associated pain and to decrease the stimulus that often results in chronic pain, which becomes a disease state in itself.

In veterinary use, the targeted delivery system and method of the invention may be useful for decreasing pain associated with orthopedic surgery or injury, or orthopedic or neurological damage associated with infection or inflammation. The method may be especially beneficial for larger animals such as horses, or smaller domestic pets such as cats and dogs.

For human medical use, the controlled administration system and method of the invention can be used to alleviate pain associated with rotator cuff injury or repair, articular joint pain or repair, temporomandibular joint disorder, tendonitis, rheumatoid and osteoarthritis, carpal tunnel syndrome, ligament pain or repair, or targeted muscular pain relief, for example. Examples of clinical indications for which the invention is appropriate include acute and chronic back and leg pain, whatever the origin. In one embodiment, the therapeutic agent is delivered in the vicinity of an irritated nerve root at dose lower than current drug dosages. The therapeutic agent could be delivered over a period of a few days to several months, depending upon the clinical indication. This directed and controlled delivery is beneficial, as certain drugs, for example TNF-inhibitors, act to reduce the infection fighting capability of the immune system and therefore can lead to infection and other adverse events. Minimizing the amount of drug (in this case therapeutic agent) and targeting a site of delivery is a significant improvement over what is currently available. Further, the versatility of the treatment options, for example, modifying the dose and delivery at will, is unique. The health care provider can be more responsive to the patient feedback or changing clinical manifestations. Other inflammatory diseases may also be treated employing the invention. Therapeutic agents can be delivered singly, in combination, in series, or simultaneously. One or multiple disc levels may be treated at the same time, with cervical, thoracic, lumbar, or multiple areas being targeted. Therapeutic agents may be applied interdiscally, adjacent to the disc, or intramuscularly. Therapeutic agents may be directed to inhibit the effects of TNF-α, cyclooxygenase 2, prostaglandin E2, mediators of inflammation such as glutamate, kinins such as bradykinin, and substance P, for example, as previously described.

The invention is useful in the prevention and treatment of osteoporosis, osteoarthritis and rheumatoid arthritis. For example, rheumatoid arthritis, particularly, is known to have an inflammatory origin, and therapeutic agents such as inhibitors of the action of TNF-α can be useful, particularly when delivered by the implant and method of the present invention, for alleviating pain associated with these conditions.

Periprosthetic osteolysis is a major complication following total joint replacement. Articulating prosthetic joint surfaces and polymethylmethacrylate (PMMA) cement may generate wear particles that cause a chronic inflammatory response and osteoclastic bone resorption (wear debris-induced osteolysis), resulting in mechanical failure of the implant. TNF and IL-1 have been shown to mediate wear debris-induced, or wear particle-induced, osteolysis. Controlled and directed delivery of TNF inhibitors according to the controlled administration system and method of the present invention at an implant site provides a method for preventing implant-associated osteolysis. Osteolysis generally, whether wear-induced or caused by other factors, because it often occurs at individual sites such as sites of joint replacement surgery, is an appropriate target for therapy using the controlled administration systems and methods of the invention. Furthermore, because TNF-α has been found to induce osteoclast-like cells and the osteoclast is the cell that resorbs bone, sustained and directed (localized) administration of TNF-α inhibitors, particularly if combined with administration of osteoinductive factors such as BMP, GDF, LMP, or a combination of both, for example, can provide both pain relief and inhibition of bone resorption.

Similarly, malignant or benign tumors of bone are often associated with bone resorption. Where tumors are removed, partially removed, or where a tumor remains, there can be considerable pain. The method and system of the invention provides a means for alleviating such pain and making a cancer patient more comfortable, as well as inhibiting bone resorption or stimulating bone growth at the site.

In one embodiment, the method of the invention can be provided by a targeted delivery system comprising an interbody or similar pharmaceutical pump, an optional catheter fluidly connected to the pump to provide a channel for at least one pharmaceutical composition to be transported from the pump to a target site, and a therapeutic quantity of at least one therapeutic agent such as, for example, a TNF inhibitor. In one embodiment, such a system may also comprise at least one modified release pharmaceutical carrier for the at least one therapeutic agent.

In an alternate embodiment, a depot can comprise at least one modified release pharmaceutical carrier for at least one therapeutic agent, and a therapeutically effective amount of at least one therapeutic agent, such as, for example, a TNF inhibitor. Targeted delivery systems can be provided as kits, comprising at least one depot provided in sterile packaging and at least one aliquot of at least one therapeutic agent in a package so that the therapeutic agent is provided in sterile form when introduced into the body. Such kits can also comprise at least one package containing at least one aliquot of at least one therapeutic agent in combination with one or more modified release pharmaceutical carriers. Kits can also provide modified release carriers containing a therapeutic agent within them, the modified release carriers being enclosed or partially enclosed within a matrix or containment device for complete or partial containment of the modified release carriers, the matrix or containment device being provided in sterile packaging and being appropriate for implantation into a target site within the body of a subject in need of therapy utilizing the at least one therapeutic agent.

A therapeutically effective amount of an anti-inflammatory agent is administered to a patient in need of said treatment. The anti-inflammatory agent is selected from the group consisting of TNF, IL-1, IL-6, IL-8, IL-12, IL-15, IL-17, IL-18, GM-CSF, M-CSF, MCP-1, MIP-1, RANTES, ENA-78, OSM, FGF, PDGF, and VEGF. A variety of anti-inflammatory agents contemplated for use in the present invention are described in United States Patent Application Publication 20030176332, which is incorporated herein by reference.

For the purposes herein, "tumor necrosis factor alpha (TNF-α)" refers to a human TNF-α molecule comprising the amino acid sequence as described in Pennica et al., Nature, 312:721 (1984) or Aggarwal et al., JBC, 260:2345 (1985). The term "human TNF-α" (abbreviated herein as hTNFα, or simply hTNF), as used herein, also is intended to refer to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) Nature 312:724-729; Davis, J. M., et al. (1987) Biochemistry 26:1322-1326; and Jones, E. Y., et al. (1989) Nature 338:225-228. The term human hTNFα is intended to include recombinant human rhTNFα, which can be prepared by standard recombinant expression methods or purchased commercially (R & D Systems, Catalog No. 210-TA, Minneapolis, Minn.). hTNFα is also referred to as TNF.

The term "TNF-α inhibitor" includes agents which interfere with a biological function of TNF-α, generally through binding-to TNF-α and neutralizing its activity. Examples of TNF-α inhibitors include etanercept (Enbrel®, Amgen), infliximab (Remicade®, Johnson and Johnson), human anti-TNF monoclonal antibody Adalimumab (D2E7/HUMIRA®, Abbott Laboratories), CDP 571 (Celltech), and CDP 870 (Celltech), as well as other compounds which inhibit TNF-α activity, such that when administered to a subject suffering from or at risk of suffering from a disorder in which TNF-α activity is detrimental, the disorder is treated. The term also includes each of the anti-TNF-α human antibodies and antibody portions described in U.S. Pat. Nos. 6,090,382; 6,258,562; 6,509,015, and in U.S. patent application Ser. Nos. 09/801,185 and 10/302,356, each incorporated by reference herein.

In some embodiments, the osteoinductive compositions or factors used in this invention as therapeutic agents further comprise a therapeutically effective amount to stimulate or induce bone growth of a substantially pure bone inductive or growth factor or protein in a pharmaceutically acceptable carrier. The preferred osteoinductive factors are the recombinant human bone morphogenetic proteins (rhBMPs), because they are available in relatively unlimited supply and do not transmit infectious diseases. Most preferably, the bone morphogenetic protein is a rhBMP-2, rhBMP-7 or heterodimers thereof. However, any bone morphogenetic protein is contemplated, including bone morphogenetic proteins designated as BMP-1 through BMP-13. BMPs are available from Genetics Institute, Inc., Cambridge, Mass. and may also be prepared by one skilled in the art, as described in U.S. Pat. Nos. 5,187,076 to Wozney et al.; 5,366,875 to Wozney et al.; 4,877,864 to Wang et al.; 5,108,922 to Wang et al.; 5,116,738 to Wang et al.; 5,013,649 to Wang et al.; 5,106,748 to Wozney et al.; and PCT Patent Nos. WO93/00432 to Wozney et al.; WO94/26893 to Celeste et al.; and WO94/26892 to Celeste et al. Osteoinductive factors included within the scope of the present invention are BMP-1, BMP-2, rhBMP-2, BMP-3, BMP-4, rhBMP-4, BMP-5, BMP-6, rhBMP-6, BMP-7-[OP-1], rhBMP-7, BMP-8, BMP-9, BMP-10, BMP-11, BMP-12, BMP-13, BMP-14, BMP-15, BMP-16, BMP-17, BMP-18, Growth and Differentiation Factors, GDF-5, Cartilage Derived Morphogenic Proteins, LIM mineralization protein, platelet derived growth factor (PDGF), transforming growth factor β (TGF-β), insulin-related growth factor-I (IGF-I), insulin-related growth factor-II (IGF-II), fibroblast growth factor (FGF), beta-2-microglobulin (BDGF II), and rhGDF-5. All osteoinductive factors are contemplated whether obtained as above or isolated from bone. Methods for isolating bone morphogenetic protein from bone are described in U.S. Pat. No. 4,294,753 to Urist and Urist et al., 81 PNAS 371, 1984.

Recombinant BMP-2 can be used at a concentration of about 0.4 mg/ml to about 2.5 mg/ml, preferably near 1.5 mg/ml. However, any bone morphogenetic protein is contemplated, including bone morphogenetic proteins designated as BMP-1 through BMP-18.

The bone growth inductive factor may be supplied as a therapeutic agent for a drug depot implant of the present invention in any suitable manner. The osteogenic factor, preferably BMP, may be provided in freeze-dried form or in any other suitable liquid or gel carrier. Any suitable medium or carrier capable of delivering the proteins to the implant is contemplated. Preferably, the medium is supplemented with a buffer solution, as is known in the art.

The term "synovial joint" refers to a moveable articulation of two or more bones. The articulation is defined by a synovial cavity, which contains a volume of synovial fluid, is lined with a synovial membrane, and is surrounded by a fibrous capsule. The opposing bone surfaces are each covered with a layer of cartilage. The cartilage and synovial fluid reduce friction between the articulating bone surfaces and enable smooth movements. Synovial joints can be further distinguished by their shape, which controls the movements they allow. For example, hinge joints act like the hinge on a door, allowing flexion and extension in just one plane. An example is the elbow between the humerus and the ulna. Ball and socket joints, such as the hip, allow movement in several planes simultaneously. Condyloid (or ellipsoid) joints, such as the knee, permit motion in more than one plane in some positions but not others. For example, no rotation is possible in the extended knee, but some rotation is possible when the knee is flexed. Pivot joints, such as the elbow (between the radius and the ulna), allow one bone to rotate around another. Saddle joints, such as at the thumb (between the metacarpal and carpal) are so named because of their saddle shape, and allow movement in a variety of directions. Finally, gliding joints, such as in the carpals of the wrist, allow a wide variety of movement, but not much distance.

Synovial joints include, but are not limited to, shoulder (glenohumeral and acromioclavicular), elbow (ulno-humeral, radio-capitellar and proximal radioulnar), forearm (radioulnar, radiocarpal, ulnocarpal), wrist (distal radioulnar, radio-carpal, ulno-carpal, mid carpal), hand (carpo-metacarpal, metocarpophalangeal, interphalangeal), spine (intervertebral), hip, knee, ankle (tibiotalar, tibiofibular), and foot (talocalcaneal, talonavicular, intertarsal, tarso-metatarsal, metatarsal-phalangeal, interphalangeal).

In some embodiments, for example, implants may be formed from hydrophilic materials, such as hydrogels, or may be formed from biocompatible elastomeric materials known in the art, including silicone, polyurethane, polyolefins such as polyisobutylene and polyisoprene, copolymers of silicone and polyurethane, neoprene, nitrile, vulcanized rubber and combinations thereof. In a preferred embodiment, the vulcanized rubber is produced by a vulcanization process utilizing a copolymer produced, for example, as in U.S. Pat. No. 5,245,098 to Summers et al., from 1-hexene and 5-methyl-1,4-hexadiene. Preferred hydrophilic materials are hydrogels. Suitable hydrogels include natural hydrogels, and those formed from polyvinyl alcohol, acrylamides such as polyacrylic acid and poly (acrylonitrile-acrylic acid), polyurethanes, polyethylene glycol, poly(N-vinyl-2-pyrrolidone), acrylates such as poly(2-hydroxy ethyl methacrylate) and copolymers of acrylates with N-vinyl pyrolidone, N-vinyl lactams, acrylamide, polyurethanes and polyacrylonitrile or may be formed from other similar materials that form a hydrogel. The hydrogel materials may further be cross-linked to provide further strength to the implant. Examples of different types of polyurethanes include thermoplastic or thermoset polyurethanes, aliphatic or aromatic polyurethanes, polyetherurethane, polycarbonate-urethane and silicone polyether-urethane. Other suitable hydrophilic polymers include naturally-occurring materials such as glucomannan gel, hyaluronic acid, polysaccharides, such as cross-linked carboxyl-containing polysaccharides, and combinations thereof.

The implants of the invention may be made of at least in part of a biocompatible material. Furthermore, in some embodiments, the implants may be made of an implantable material, such as a material suitable for implantation in bone, implantation in cartilage, and/or implantation in other biomaterials in a joint. In particular, the implant may be formed at least in part of a material that can maintain its integrity during implantation. This may help prevent leakage of a drug in the carrier through a crack or fissure in the implant. In some embodiments, the implant reservoir may be constructed from a metal, such as titanium, nickel titanium, stainless steel, anodized aluminum, or tantalum, or a plastic, such as polyethylene, nylon, or polyurethane. The implant may also include a material or modified material to allow for osseous integration of the implant—i.e., bone ingrowth. Other suitable materials will be apparent to one of ordinary skill in the art. Moreover, combinations of materials may be used.

The implants of the invention may be provided with surface features defined in their outer surfaces. For example, a projection may be formed on the end walls instead of a slot. Such a projection may form a straight, flat-sided shape, an elliptical eminence, a bi-concave eminence, a square eminence, or any other protruding shape which provides sufficient end-cap or tool engaging end strength and drive purchase to allow transmission of insertional torque without breaking or otherwise damaging the eminence. Yet other surface features can be defined on the implant. As mentioned above, the outer surface of the implant may define barbs or other surface features that may stabilize the drug depot implant interface with tissue and reduce micromotion.

The drug depot implants of the present invention may be designed for placement and location within or near the synovial joint, spinal disc space, spinal canal or the surrounding soft tissue. In some embodiments, the contemplated placement and location areas of the drug depot implants within the desired location of the subject will not cause damage to the bone, cartilage surface or tissue, as it may be placed and secured using an anchoring device.

In some embodiments, placement of the device in a patient may be an intra-articular region of a synovial joint where there is no interfacing articular cartilage. It may be located, for example, within the inside of the knee capsule that is non-load-bearing and removed from the articulation surface of the synovial joint. The device may be attached within the synovial joint, allowing for continuous exposure to synovial fluid flow and resulting release of anti-inflammatory or osteogenic therapeutic agents, without damaging the articular surface that is in apposition during range of motion of the given joint.

According to another embodiment of the present invention, the therapeutic agent, e.g., anti-inflammatory agent or osteoinductive factor, can be packaged into gas-filled lipid-containing microspheres. The gas-filled lipid-containing microspheres may further comprise biocompatible polymers on their outer surfaces. The present invention provides that the therapeutic agent may also be contained in a freeze dried state within the microsphere to preserve it's stability and activity over an extended period of time. Similarly, the present invention also provides that the therapeutic agent may be contained in a freeze dried state within the depots to preserve it's stability and activity over an extended period of time.

Non-limiting examples of suitable gases are air, nitrogen, carbon dioxide, oxygen, argon, fluorine, xenon, neon, helium, or any and all combinations thereof. Furthermore, various fluorinated gaseous compounds, such as various perfluorocarbon, hydrofluorocarbon, and sulfur hexafluoride gases may be utilized in the preparation of the gas filled microspheres.

For the biocompatible lipid materials, it is preferred that such lipid materials be what is often referred to as "amphiphilic" in nature (i.e., polar lipid), by which is meant any composition of matter which has, on the one hand, lipophilic, i.e., hydrophobic properties, while on the other hand, and at the same time, having hydrophilic properties. The lipid may alternatively be in the form of a monolayer, and the monolayer lipids may be used to form a single monolayer (unilamellar) arrangement. Alternatively, the monolayer lipid may be used to form a series of concentric monolayers, i.e., oligolamellar or multilamellar, and such arrangements are also considered to be within the scope of the invention.

Non-limiting examples of suitable lipids are fatty acids, lysolipids, phosphatidylcholine with both saturated and unsaturated lipids, dimyristoylphosphatidylcholine, dipentadecanoylphosphatidylcholine, dilauroylphosphatidylcholine, dipalmitoylphosphatidylcholine (DPPC), distearoylphosphatidylcholine (DSPC), phosphatidylethanolamines, phosphatidylserine, phosphatidylglycerol, phosphatidylinositol, sphingolipidsglycolipids, glucolipids, sulfatides, glycosphingolipids, phosphatidic acids, palmitic acid, stearic acid, arachidonic acid, oleic acid, lipids bearing polymers, lipids bearing sulfonated mono-, di-, oligo- or polysaccharides, cholesterol, cholesterol sulfate and cholesterol hemisuccinate, tocopherol hemisuccinate, lipids with ether and ester-linked fatty acids, polymerized lipids, diacetyl phosphate, dicetyl phosphate, stearylamine, cardiolipin, phospholipids with short chain fatty acids of 6-8 carbons in length, synthetic phospholipids with asymmetric acyl chains (e.g., with one acyl chain of 6 carbons and another acyl chain of 12 carbons), ceramides, non-ionic liposomes, polyoxyethylene fatty alcohols, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oil, polyoxyethylene-polyoxypropylene polymers, and polyoxyethylene fatty acid stearates; sterol aliphatic acid esters including cholesterol sulfate, cholesterol butyrate, cholesterol iso-butyrate, cholesterol palmitate, cholesterol stearate, lanosterol acetate, ergosterol palmitate, and phytosterol n-butyrate; sterol esters of sugar acids, esters of sugar acids and alcohols, esters of sugars and aliphatic acids, saponins, glycerol dilaurate, glycerol trilaurate, glycerol dipalmitate, glycerol and glycerol esters, longchain alcohols, digalactosyldiglyceride, 6-(5-cholesten-3.beta.-yloxy)hexyl-6-amino-6-deoxy-1-thio-.beta.-D-galacto pyranoside, 6-(5-cholesten-3.beta.-yloxy)hexyl-6-amino-6-deoxyl-1-thio-.alpha.-D-manno pyranoside, 12-(((7'-diethylaminocoumarin-3-yl)carbonyl)methylamino)-octadecanoic acid, N→12-(((7'-diethylaminocoumarin-3-yl)carbonyl)methyl-amino) octadecanoyl!-2-aminopalmitic acid, cholesteryl)4'-trimethylammonio)butanoate, N-succinyldioleoylphosphatidylethanolamine, 1,3-dipalmitoyl-2-succinylglycerol, and/or combinations thereof.

Polymers suitable for this embodiment of the present invention can be natural, semi-synthetic or synthetic. Exemplary natural polymers suitable for use in the present invention include naturally occurring polysaccharides, such as for example, arabinans, fructans, fucans, galactans, galacturonans, glucans, mannans, xylans (such as, for example, inulin), levan, fucoidan, carrageenan, galatocarolose, pectic acid, pectin, amylose, pullulan, glycogen, amylopectin, cellulose, dextran, pustulan, chitin, agarose, keratan, chondroitan, dermatan, hyaluronic acid, alginic acid, xanthan gum, starch and various other natural homopolymer or heteropolymers such as those containing one or more of the following aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Exemplary semi-synthetic polymers include carboxymethylcellulose, hydroxymethylcellulose, hydroxypropylmethylcellulose, methylcellulose, and methoxycellulose. Exemplary synthetic polymers suitable for use in the present invention include polyethylenes (such as, for example, polyethylene glycol, polyoxyethylene, and polyethylene terephthlate), polypropylenes (such as, for example, polypropylene glycol), polyurethanes (such as, for example, polyvinyl alcohol (PVA), polyvinylchloride and polyvinylpyrrolidone), polyamides including nylon, polystyrene, polylactic acids, fluorinated hydrocarbons, fluorinated carbons (such as, for example, polytetrafluoroethylene), and polymethylmethacrylate, and derivatives thereof.

The gas-filled lipid containing microspheres of the present embodiment can be prepared, for example, by shaking an aqueous solution comprising a lipid in the presence of a gas at a temperature below the gel state to liquid crystalline state phase transition temperature of the lipid. The shaking must be of sufficient force to result in the formation of microspheres, particularily stabilized microspheres. The shaking may be by swirling, such as by vortexing, side-to-side, or up-and-down motion. Different types of motion may be combined. Also, the shaking may occur by shaking the container holding the aqueous lipid solution, or by shaking the aqueous solution within the container without shaking the container itself. It is preferred that the motion be reciprocating in the form of an arc between about 2 degrees and about 20 degrees, more preferably, around 6.5 degrees. It is contemplated that both the arc and the rate of reciprocation are critical to determining the amount and size of the gas and gaseous precursor filled microspheres formed. It is a preferred embodiment of the present invention that the number of reciprocations, i.e., full cycle oscillations, be within the range of about 1000 and about 20,000 per minute.

It would be apparent to a person skilled in the art that other techniques of making the gas-filled lipid-containing microspheres of the present embodiment are available. One can create such microspheres by using freeze-thaw, as well as techniques such as sonication, chelate dialysis, homogenization, solvent infusion, microemulsification, spontaneous formation, solvent vaporization, French pressure cell technique, controlled detergent dialysis, and other known techniques.

The gas and gaseous precursor filled microspheres made by the method described above can then be sized by optical microscopy. It should be determined that the largest size of the microspheres ranges from about 50 to about 60 µm and the smallest size detected should be about 8 µm. The average size should range from about 15 to 20 µm. The gas and gaseous precursor filled microspheres may then be filtered through an 8, 10 or 12 µm "NUCLEPORE" membrane using a Swin-Lok Filter Holder, (Nuclepore Filtration Products, Costar Corp., Cambridge, Mass.) and a 20 cc syringe (Becton Dickinson & Co., Rutherford, N.J.). The membrane may be a 10 or 12 µm "NUCLEPORE" membrane (Nuclepore Filtration Products, Costar Corp., Cambridge, Mass.). The 10.0 µm filter is placed in the Swin-Lok Filter Holder and the cap tightened down securely. The lipid-based microsphere solution is shaken up and it is transferred to the 20 cc syringe via an 18 gauge needle. Approximately 12 ml of gas filled foam solution may be placed in the syringe, and the syringe screwed onto the Swin-Lok Filter Holder. The syringe and the filter holder assembly are inverted so that the larger of the gas and gaseous precursor filled microspheres can rise to the top. Then, the syringe is gently pushed up and the gas and gaseous precursor filled microspheres are filtered in this manner.

The survival rate (the amount of the gas and gaseous precursor filled microspheres that are retained after the extrusion process) of the gas and gaseous precursor filled microspheres after the extrusion through the 10.0 µm filter is about 83-92%. Before hand extrusion, the volume of foam is about 12 ml and the volume of aqueous solution is about 4 ml. After hand extrusion, the volume of foam is about 10-11 ml and the volume of aqueous solution is about 4 ml.

The optical microscope may be used again to determine the size distribution of the extruded gas and gaseous precursor filled microspheres. It is determined that the largest size of the microspheres ranges from about 25 to about 30 µm and the smallest size detected is about 5 µm. The average size ranges from about 8 to about 15 µm.

Specific embodiments according to the methods of the present invention will now be described in the following non-limiting examples. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

In one specific application, the present invention contemplates drug depot implants as depicted in FIG. 1. FIG. 1 is a cross-sectional view of a rod-shaped drug depot implant 10 comprising one or more small barbs 12 that serve as anchoring devices to minimize migration of the implant in a patient's tissue once implanted. In the following, the term "rod-shaped" is intended to indicate any shape with a longitudinal axis—i.e., is longer along one direction than in other directions; the cross-sectional shape across the longitudinal axis may be any shape, but is preferably elliptical or circular. The implant 10 comprises a rod-shaped (or bullet-shaped) body 14, which is made from a biodegradable material. The non-biodegradable body could be a porous hollow chamber filled with the therapeutic agent alone or incorporated into a degradable polymer. It may be desirable to make it non-degradabel to be able to retriev it after has released it's contents. Or the non-biodegradable body could be a small pump that pushed the contents out pores, port(s), or a cannula. Non-limiting examples of suitable biodegradable materials for the body 14 include polyorthoesters (POE), polylacticglycolic acid (PLGA) polysacharides (Saber technology), polycapralactone, polyfumarate, tyrosine polycarbonate, etc. The body 14 is solid, and a therapeutic agent 16 is dispersed throughout the material that forms the body 14. The dispersal of the therapeutic agent 16 may be even throughout the body 14. Alternatively, the concentration of the therapeutic agent may vary as a function of the distance from the longitudinal centerline 18 of the body 14, or as a function of a distance along the longitudinal centerline 18. As the biodegradable material of the body 14 degrades within the tissue, the therapeutic agent 16 is released. Suitable sustained release materials may be used for the body 14 to carry the one or more therapeutic agents 16 and control the release of the therapeutic agent(s) 16. For example, microspheres may be used to encapsulate the therapeutic agent; the therapeutic agent-containing microspheres are then dispersed through the body 14. The one or more barbs 12 serve as an anchoring system, and are designed to permit forward translational movement of the body 14 along the longitudinal axis 18, while retarding backward translational movement. Specifically, the barbs 12 extend from the body 14 and point backwards along the longitudinal axis 18. The barbs 12 may be made from the same material from which the body 14 is made, or from a different material. For example, the barbs 12 may be made from a secondary material that degrades more slowly than the primary material of the body 14, and attach to a core of such secondary material that runs through the longitudinal centerline 18 of the body 14. The present invention provides other designs for gradient variations in biodegradabilitiy to hold the depot in place while the secondary material releases it's contents. The barbs could be a "snap-on" component that fits over the depot containing the therapeutic agent. In this embodiment the manufacturing of the drug loaded depot is made easier instead of having to injection mold the barbs into the depot. The barbs 12 may be axially aligned or circumferentially spaced in relation to each other about the drug depot implant 10. In certain embodiments, the implant 10 may be designed to be affixable within a joint. The implant 10 may have a width from about 1 mm to about 6 mm, and a length from about 5 mm to about 20 mm. Selection of suitable lengths and widths for the device 10 will depend upon the targeted implant site, and is well within the abilities of those having ordinary skill in the art.

Figure 2:
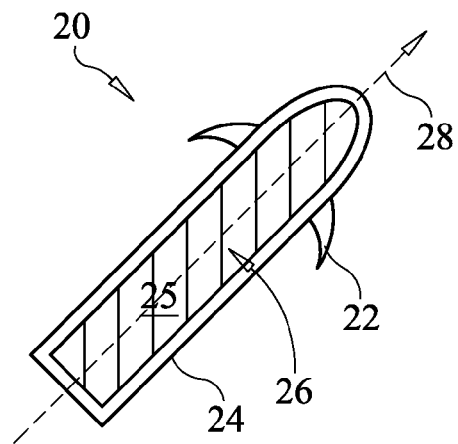
FIG. 2 is a cross-sectional view of an alternative embodiment of a drug depot implant.

FIG. 2 is a cross-sectional view of another implant 20. As with the previous example, the implant 20 comprises one or more barbs 22 that permit forward motion of the implant 20, while retarding backward motion, thus serving as an anchoring system to anchor the implant 20 within the targeted delivery site. The implant 20 comprises a rod-shaped shell 24 that is made from a non-biodegradable material, such as polyethylene, delrin, polyurethane. Alternatively, the shell 24 may be made from a bio-degradable material that degrades relatively slowly within the implant site; suitable materials include [POE, PLGA, PLA, PGA, all the other standard degradable polymers. The shell 24 forms a cavity 25, and one or more therapeutic agents 26 are disposed within the cavity 25. The therapeutic agents 26 may be, for example, in freeze-dried form, dispersed in a carrier, contained within microspheres, or packed in any other suitable manner within the cavity 25. The shell 24 is permeable to the therapeutic agent 26, however packed, so that the therapeutic agent 26 can diffuse through the shell 24 and into the surrounding tissue. For example, in the case where the shell 24 holds therapeutic agent-containing microspheres, the shell 24 may comprise a plurality of pores through which the microspheres may pass to subsequently release the therapeutic agent in or near the targeted tissue; alternatively, the microspheres may release the therapeutic agent within the shell 24, and then the therapeutic agent may diffuse through the shell 24 to to the targeted tissuethrough pores or hydrolocaclly pumped out of the device. The diffusion rate of the therapeutic agent 26 may be controlled by the thickness of the shell 24, by the number and diameter of the pores within the shell 24, . . . . The concentration of the therapeutic agent or the medium (gelatin, POE, PLGA, etc.) in which the therapeutic agent is embedded. The barbs 22 may be made from the same material as the shell 24, and may be disposed in any suitable manner about the outer surface of the shell 24. If the shell 24 is made from a biodegradable material, the type and thickness of the material used should be sufficient to ensure that all, or nearly all, of the therapeutic agent 26 has dispersed into the surrounding tissue before the integrity of shell 24 is substantially compromised.

Figure 3:
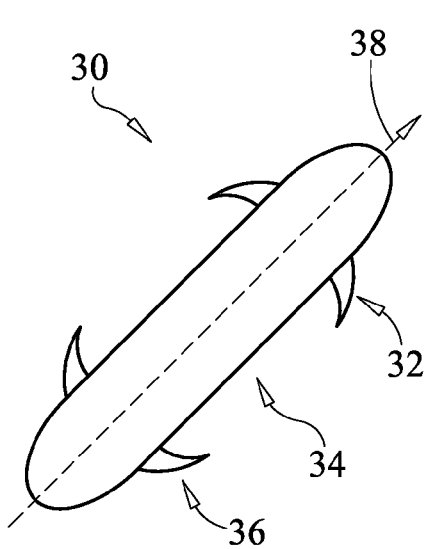
FIG. 3 is a side view of another embodiment of a drug depot implant.

FIG. 3 is a side view of another implant 30. The implant 30 may be solid, as in the implant 10, or shell-like, as in the implant 20. The implant 30 has a rod-shaped outer surface 34 from which a therapeutic agent, contained internally of the outer surface 34, diffuses, as discussed above. Extending from the outer surface 34 are one or more first barbs 32 and one or more second barbs 36. The first barbs 32 point backwards along the longitudinal axis 38 to prevent backward movement of the implant 30 (i.e., movement opposite to the direction indicated by longitudinal centerline arrow 38); the second barbs 36 point forwards along the longitudinal axis 38 to prevent forward movement of the implant 30 (i.e., movement along the longitudinal centerline arrow 38). The barbs 32, 36 thus serve as an anchoring system to keep the implant 30 at the targeted delivery site; that is, the anchoring systems prevent both forward and backward translational movement of the implant 30.

Figure 4:
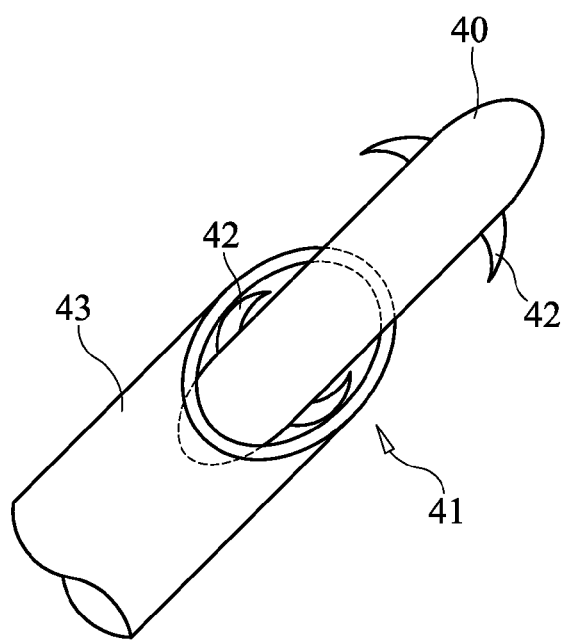
FIG. 4 shows a targeted delivery device and a drug depot implant.

The barbs 12, 22, 32, 36 in the above examples may be flexible; that is, they may be compressible towards the centerline of the longitudinal axis 18, 28, 38. This may assist in the targeted delivery of the implant 10, 20, 30. For example, as shown in FIG. 4, an implant 40 may be released at a target site by a targeted delivery system 41, which may be a catheter, a syringe, or any other suitable device. As shown, the targeted delivery system 41 may include a cannula 43 in which the implant 40 is disposed. The implant 40 has flexible barbs 42 that extent as they exit from the cannula 43.

Figure 5:
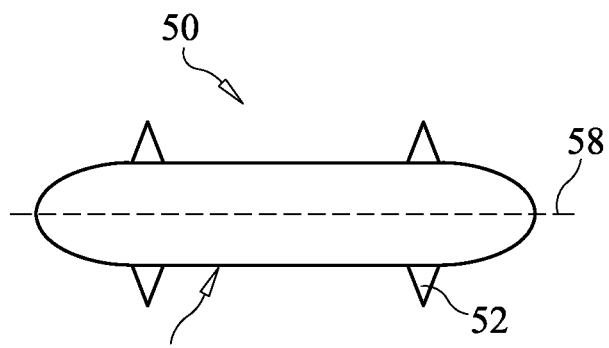
FIG. 5 is a side view of another drug depot implant.

FIG. 5 is a side view of another embodiment implant 50. The implant 50 has a rod-shaped outer surface 54 from which elutes a therapeutic agent contained therein. Extending from the outer surface 54 is one or more extensions 52 adapted to prevent both forward and backward translational movement of the implant 50, and which thus serve as an anchoring system to keep the implant 50 at the targeted delivery site. The extensions 52 may be flexible, and hence may extend once released from a targeted delivery device. The extensions 52 point substantially 90 degrees away from the longitudinal axis 58. The anchoring system provided by the extensions 52 may also prevent rotational movement of the implant 50.

Figure 6:
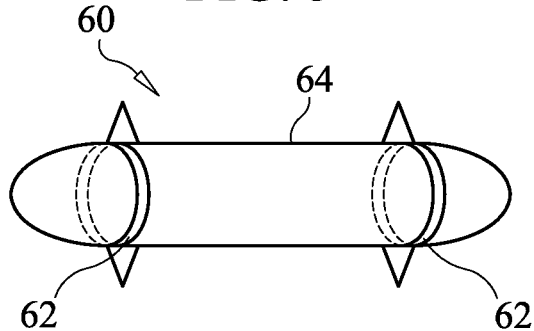
FIG. 6 shows a drug depot implant with a first embodiment radiographic marker.
Figure 7:
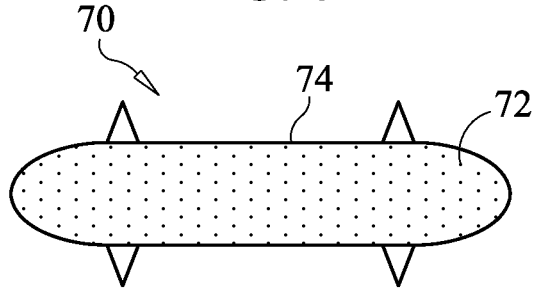
FIG. 7 shows a drug depot implant with a second embodiment radiographic marker.

Implants of the present invention may be provided radiographic markers that assist in the imaging of the implants, and hence in the targeted delivery of the implants. The radiographic markers may be made from any suitable material, as previously discussed, and may be, for example, ring-shaped, or dispersed as small pellets throughout the implant. An implant 60 utilizing ring-shaped radiographic markers is depicted in FIG. 6. As shown, one or more radiographically active rings 62 are positioned in or on the body 64 of the implant 60. Each ring 62 is placed at a predetermined position within the body 64, and thus when imaged enables a physician to determine the position and orientation of the implant 60. FIG. 7 presents another possible embodiment for radiographic markers as applied to an implant of the present invention. An implant 70 comprises a body portion that holds, and elutes, the therapeutic agent. Regularly dispersed throughout, or on, the body portion 74 are small beads 72 of a radiographically active substance. Imaging of the beads 72 provides a clear indication of the position and orientation of the body portion 74 within the target tissue. Alternatively, the beads 72 may be disposed in or on the body portion 74 according to a predetermined pattern; imaging of this pattern presented by the beads 72 will similarly provide solid reference for the position and orientation of the body portion 74.

Figure 8:
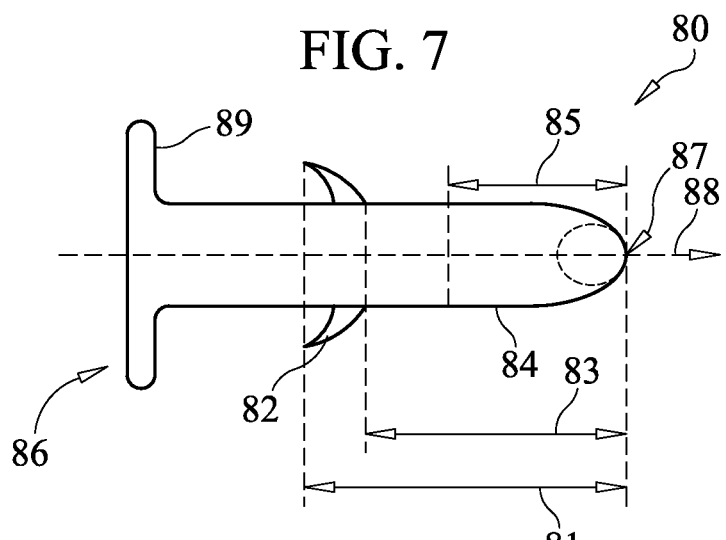
FIG. 8 is a side view of an alternative embodiment of a drug depot implant.

FIG. 8 is a side view of another implant 80. The implant 80 has a rod-shaped body portion 84, which may be tapered, from which extends a first anchoring system 82 and a second anchoring system 86 that secure the implant 80 within the targeted tissue location. The first anchoring system 82 is configured as one or more barbs 82, which point backwards with respect to the forward (or insertion) direction indicated by longitudinal centerline arrow 88. The barbs 82 thus prevent the implant 80 from backing out of the implant site. The barbs 82 may be flexible. The second anchoring system 86 is an end cap 86 that is adapted to abut against a tissue plane. A forward surface 89 of the end cap 86 contacts the tissue plane, and thus prevents forward translational movement, as indicated by centerline arrow 88, of the implant 80. Both the barbs 82 and the end cap 86 may be made from the same material as the body portion 84. The body portion 84 may be hollow or solid, and may or may not be biodegradable, as described previously. The body portion 84 contains, and elutes, the desired therapeutic agent. Although the therapeutic agent may be dispersed throughout the body portion 84, as well as throughout the barbs 82 and end cap 86, it may be desirable to dispose the therapeutic agent only within a forward region of the body portion 84. For example, it may be desirable to dispose the therapeutic agent only within the forward two-thirds of the body portion 84, as indicated by arrow 81. Alternatively, it may be desirable to have the therapeutic agent in only the forward half of the body portion, as indicated by arrow 83, or only the forward third, as indicated by arrow 85. Indeed, it may be desirable to have the therapeutic agent disposed only within a tip region 87 of the body portion 84. Hence, depending upon the region 81, 83, 85, 87 selected, the therapeutic agent will only elute from that specific region 81, 83, 85, 87 of the implant 80. The forward end 81, 83, 85, 87 of the body portion 84 that contains the therapeutic agent may be termed the active end of the implant 80. The end cap 86 may be formed with the body portion 84, i.e., be monolithic with the body portion 84, or may be provided as a separate element. If provided as a separate element, the end cap 86 and body portion 84 should have corresponding mating elements that enable a physician to attach the end cap 86 to the body portion 84 after the body portion 84 has been deployed at a targeted tissue site. Any suitable mating system may be used such as for example, mechanical snap-on or threaded fixation.

Figure 9:
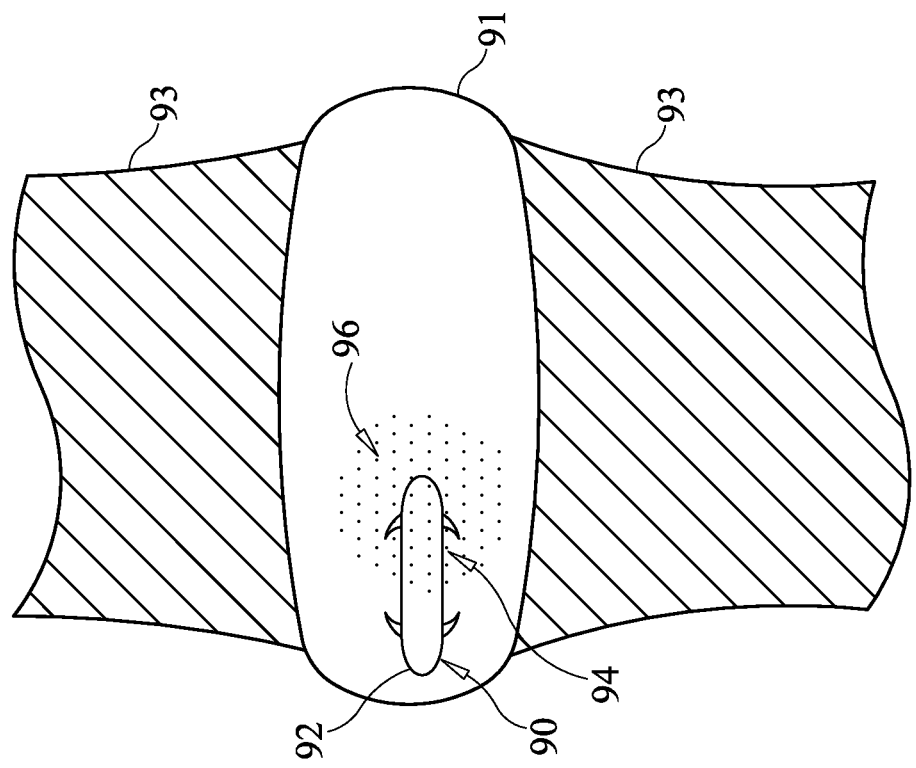
FIG. 9 illustrates the drug depot implant of FIG. 9 deployed in a disk.

As shown in FIG. 9, an implant 90 of the instant invention may be disposed in a disc 91 to alleviate discogenic pain. A disc 91 to be treated is sandwiched between two vertebrae 93. The implant 90 is inserted into the interior region of the disc 91, such as the annular fibrosus or nucleus pulposus of the disc 91. This embodiment is achieved for example as shown in FIG. 4, through a hollow cannula. The cannula is withdraw, deploying the barbs. The implant 90 has an anchoring system 92 that extends from the implant 90 to keep the implant 90 firmly constrained to the targeted tissue site, preventing forward and backwards movement of the implant 90 within the disc 91. The implant 90 also has an active region 94 that elutes a therapeutic agent 96 into the disc 91. The concentration gradient of the eluted therapeutic agent 96 may extend from 1 cm to as far as 5 cm from the active region 94 of the implant 90.

Figure 10:
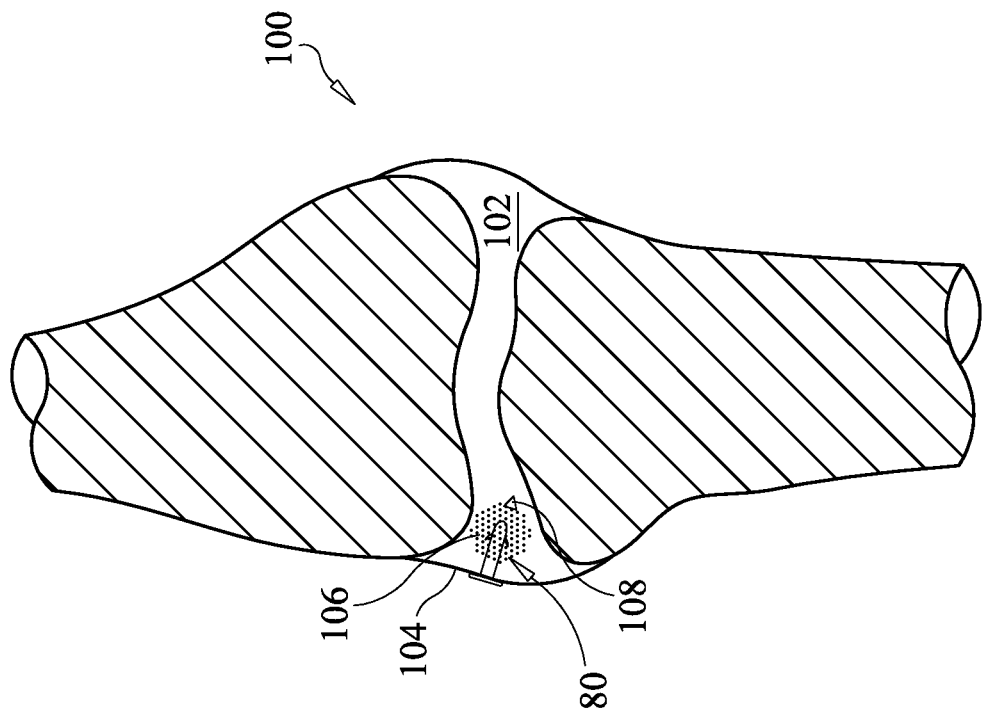
FIG. 10 illustrates the drug depot implant of FIG. 8 deployed in a joint.

The implant 80 of FIG. 8 is shown deployed in the synovial cavity 102 of a synovial joint 100 in FIG. 10. The joint 100 depicted is an idealized synovial joint but roughly approximates the femur-tibia articulation at the knee. Exemplary placement of the implant 80 is indicated. In this example, the placement of the implant 80 is in the joint and is remote from the bone. As shown, the forward surface 89 of the end cap 86 abuts against the synovial membrane 104, thus preventing forward movement of the implant 80 into the joint 100. Similarly, the barbs 82 prevent the implant 80 from backing out of the joint 100. An active end 106 of the implant 80 elutes a therapeutic agent 108 into the synovial fluid of the cavity 102.

Figure 11:
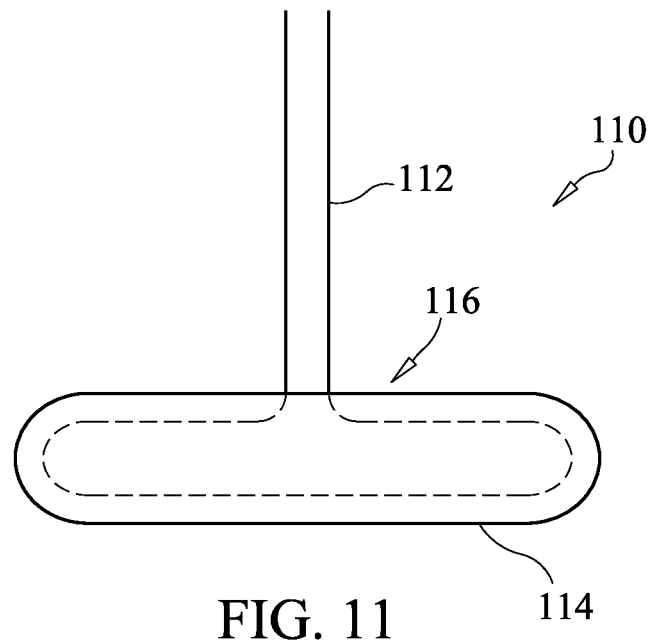
FIG. 11 is a side view of another drug depot implant.

FIG. 11 is a side view of another implant 110. The implant 110 comprises a tapered, rod-shaped body portion 114 and a suture 112 that extends from the body 114. The body 114 may be hollow or solid, as previously described, and made from a biodegradable or non-biodegradable material. The body 114 contains, and elutes, a therapeutic agent. The entire body 114 may be active (i.e., elute the therapeutic agent), or instead may have an active region in a predetermined position, as indicated earlier for other embodiments. The suture 112 may be made from a biodegradable or non-biodegradable material. If made from a biodegradable material, it may be desirable to select a material for the suture 112 that degrades significantly slower than the body 114. As shown, the suture 112 enters from a central region 116 of the body 114, substantially circumnavigates the body 114 and then exits from the central region 116. The suture 112, extending from the body portion 114, serves as an anchoring system for the implant 110. By tying the suture 112 onto adjacent tissue, it is possible to securely retain the implant 110 at a targeted tissue site, and hence prevent translational movement of the implant 110 within or from the targeted tissue site.

Figure 12:
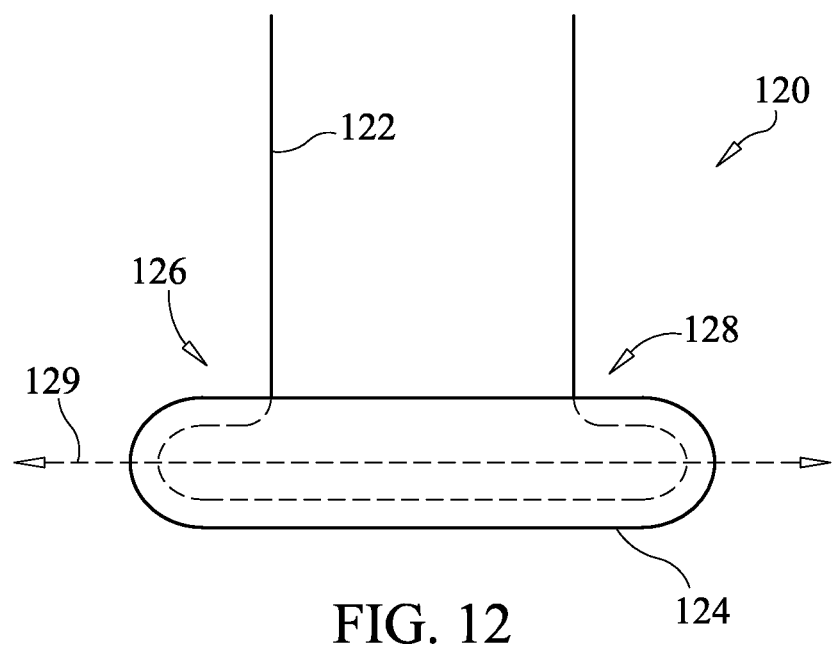
FIG. 12 is a side view of an alternative drug depot implant.

FIG. 12 shows an another implant 120 that similarly utilizes a suture 122. As in the implant 110, the suture 124 may traverse just under the body portion 124. In the implant 120, however, the suture 122 enters the body portion 124 from a first end region 126 of the body 124 and exits from a second end region 128 of the body 124. The end regions 126, 128 may include, for example, the outer third of the body portion 124, with respect to the longitudinal axis 129.

Another embodiment implant 130 is shown in FIG. 13. For the implant 130, the suture 132 enters at or near a first endpoint 136 of the body 134, traverses within the body 134 substantially along the longitudinal centerline 139, and exits from, or near, a second endpoint 138 of the body 124. The endpoints 136, 138 are defined by the longitudinal centerline 139 of the body 134.

It is contemplated that the several drug depot designs 110, 120, 130 may be used in joint capsules, with the sutures 112, 122, 132 being used to retain the depot 110, 120, 130 up against the inside of the joint capsule. FIG. 14 shows, for example, deployment of the implant 110 of FIG. 11 in a synovial joint 140. The bullet-shaped tip of the body 114 eases insertion of the implant 110 through the joint capsule tissue 142 and minimizes tissue disruption. A very small hole is made in the joint capsule 142 with a blunt probe, and then the tapered rod 114 is slowly pushed through this hole, slowly stretching the tissues apart to minimize tissue tearing. Once the rod 114 is fully inserted, the hole in the joint capsule 142 closes upon itself. The suture 112 embedded in the rod 114 is left passing through the capsule 142 so that it can be pulled taught and knotted up against the outside of the joint capsule 142, forcing the depot 110 up against the inside of the joint capsule 142. Having the depot 110 up against the inside of the joint capsule 142 will prevent the depot 110 from interfering with normal joint 140 motion.

FIG. 15 shows the implant 120 of FIG. 12 deployed in a synovial joint 150. The suture 122 exits from two points in the joint capsule 152. The ends of the suture 122 may be tied off together or separately. This design offers the advantage of holding the depot 120 up against the inside of the joint capsule 152 without rotating and potentially interfering with motion of the joint 150.

Several implant designs are contemplated for use in intervertebral disc and joint capsules that comprise bead-shaped depots strung together along a suture. Such an embodiment implant 160 is depicted in FIG. 16. Analogous to the embodiments discussed earlier, the beads 164 may be in the form of a solid, biodegradable material, such as a polymer, loaded with a therapeutic agent; alternatively, the beads 164 may form a cavity that is packed with the therapeutic agent, and which may diffuse through the walls of the cavity. The beads 164 elute the therapeutic agent when disposed within the targeted tissue site. The beads 164 may be from XXXX to YYYY in diameter. The suture 162 may be either a degradable or a non-degradable material. Extending from an end of the implant 160 is an optional needle or barb 166 to serve as an anchoring device that retains the strand 160 within the targeted tissue site, such as a disc or joint capsule.

Figure 19:
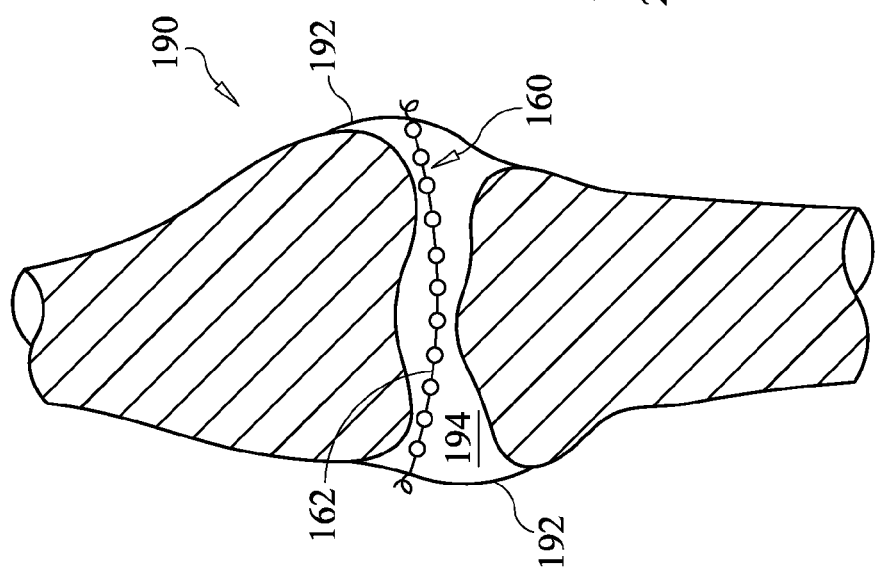
FIG. 19 shows the drug depot implant of FIG. 16 deployed in a joint.

This implant 160 optimally positions the therapeutic agent eluting beads 164 along the route of inflamed tissue, resulting in a more effective distribution of the therapeutic agent and clinical effectiveness. As shown in FIG. 17, the strand 160 may be implanted by inserting a cannula 170 containing the strand 160 of beads 164 as far as desired inside, for example, a disc, joint, or soft tissue, and then deploying the barb 166 into the soft tissue (such as the annulus) and slowly retracting the cannula 170, which will result in the implant 160 being pulled from the cannula 170. By fixing, for example, the leading edge of the implant 160, the anchoring device 166 retains the beads 164 at the location where the therapeutic agent is desired. FIGS. 18 and 19 illustrate the implant 160 being deployed in targeted tissue sites. A very small hole is made in an intervertebral disc 180 or in a joint capsule 192 with a blunt probe, through which a cannula is inserted to implant the string 160 of beads 164. For example, as shown in FIG. 18, the implant 160 may be deployed inside a disc 180, with the anchoring device 166 embedded within the annular fibrosus of the disc 180. The beads 164 may extend inside the disc 180, and then externally along the nerve root 182. As shown in FIG. 19, the implant 160 may be deployed transverse across a joint 190, resulting in a more uniform distribution of the therapeutic agent within the synovial cavity 194 of the joint 190. The suture 162 at the ends of the implant 160 may be tied off to the joint capsule 192 to anchor the implant 160 within the joint 190.

Figure 21:
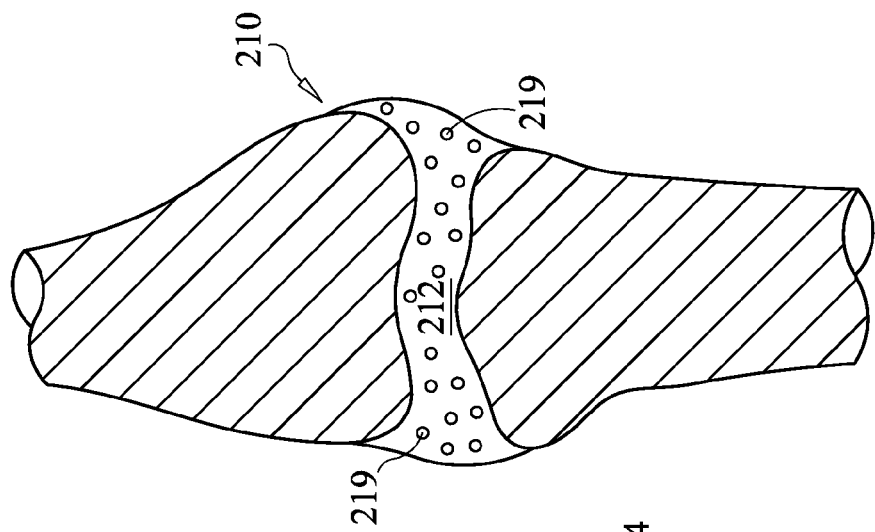
FIG. 21 illustrates delivery of a therapeutic agent to a synovial cavity utilizing microspheres.
Figure 20:
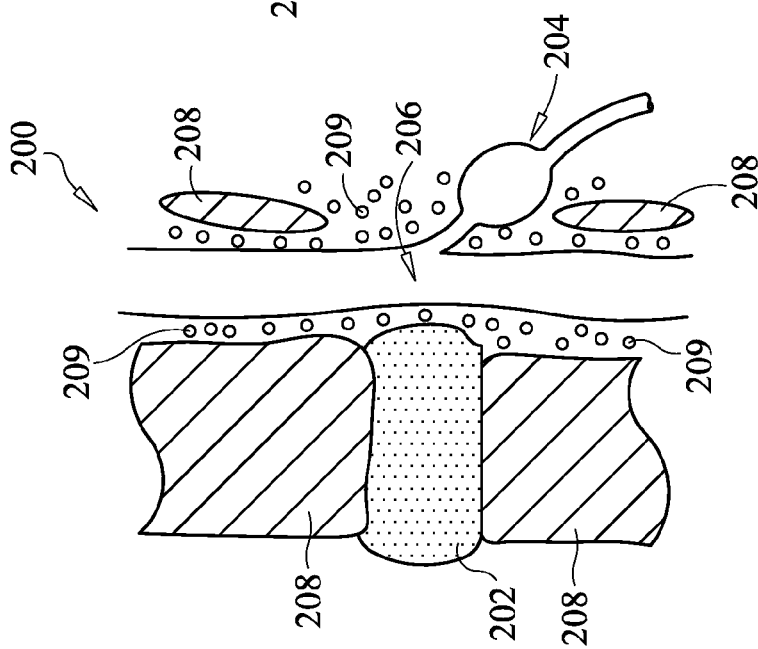
FIG. 20 illustrates delivery of a therapeutic agent to a spinal canal and surrounding soft tissue utilizing microspheres.

The present invention provides another method for administering a therapeutic agent to a targeted tissue site. As shown in FIG. 20, the targeted tissue site may be a spinal canal 200 or tissue surrounding the spinal canal 200, such as a disc 202 or a nerve root 204. The spinal cord 206 runs through the spinal canal 200, which is provided by the vertebrae 208. As discussed earlier, microspheres 209 encapsulating the desired therapeutic agent may be formed in a known manner. These microspheres 209 may then be deployed into the spinal canal 200, such as by injecting a carrier containing the microspheres 209 into the spinal canal 200. The microspheres 209 then elute the therapeutic agent into the spinal canal 200. The microspheres 209 may disperse to the surrounding tissue, such as the nerve root 204 or the disc 202. Alternatively, to provide therapeutic treatment primarily to the disc 202 alone, the therapeutic-containing microspheres 209 may be directly injected into the disc 202. As shown in FIG. 21, microspheres 219 loaded with a therapeutic agent may be injected into a synovial cavity 212 to treat a joint 210. A syringe or similar device may be used to deploy the microspheres 219 into the joint cavity 212.

Microspheres, much like a fluid, may disperse relatively quickly, depending upon the surrounding tissue type, and hence disperse the therapeutic agent. In some situations, this may be desirable; in others, it may be more desirable to keep the therapeutic agent tightly constrained to a well-defined target site. The present invention contemplates the use of adherent gels to so constrain dispersal of the therapeutic agent. These gels may be deployed, for example, in a disc space, in a spinal canal, or in surrounding tissue, or in a joint space, such as a synovial cavityIn this embodiment the gel is an adherent and/or settable gel in order to stay in place within a joint space.

In one embodiment, a depot comprises an adherent gel comprising a therapeutic agent that is evenly distributed throughout the gel. The gel may be of any suitable type, as previously indicated, and should be sufficiently viscous as to prevent the gel from migrating from the targeted delivery site once deployed; the gel should, in effect, "stick" to the targeted tissue site. The gel may, for example, solidify upon contact with the targeted tissue, or after deployment from a targeted delivery system. The targeted delivery system may be, for example, a syringe, a catheter or any other suitable device. The targeted delivery system may inject or spray the gel into or on the targeted tissue site. The therapeutic agent may be mixed into the gel prior to the gel being deployed at the targeted tissue site. The gel may be biodegradable. For the non-settable gels, they may be sold premixed and just delivered, but for the adherent and/or settable gel, they may need to be two component delivery systems that mix the two components upon injection to activate a chemical process to cause them to stick or set up.

Figure 22:
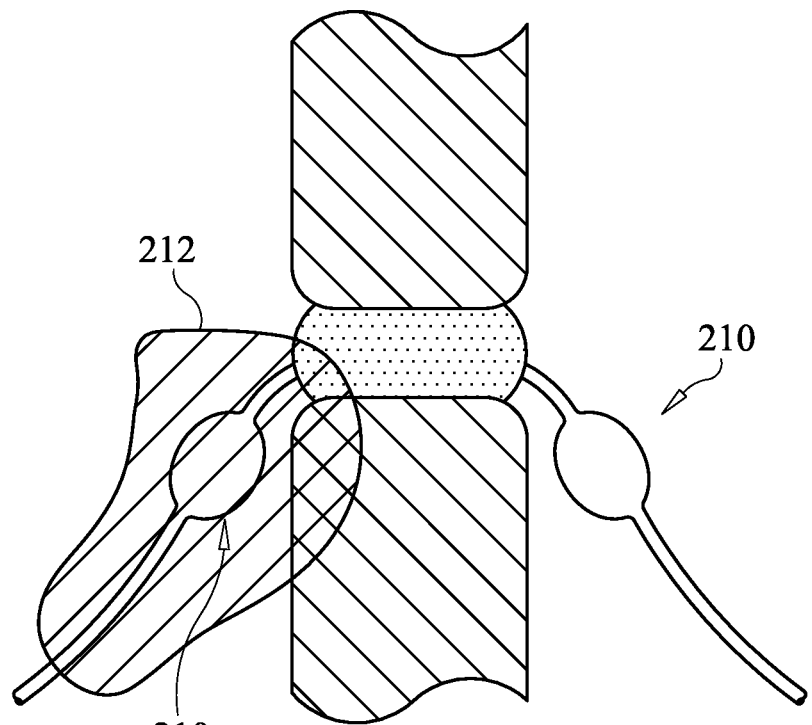
FIG. 22 illustrates delivery of a therapeutic agent to soft tissue surrounding a spinal canal utilizing a gel.

FIG. 22 illustrates a gel 212, imbued with a therapeutic agent, deployed around a targeted tissue site, a nerve root 210. The gel 212, either viscous or solid once deployed, keeps the therapeutic agent closely bound to the nerve root 210, thereby providing a therapeutically effective dosage of the therapeutic agent to the nerve root 210, with the dosage gradient rapidly falling off outside of the region of the gel 212. The therapeutic agent is therefore tightly targeted at the nerve root 210.

Figure 23:
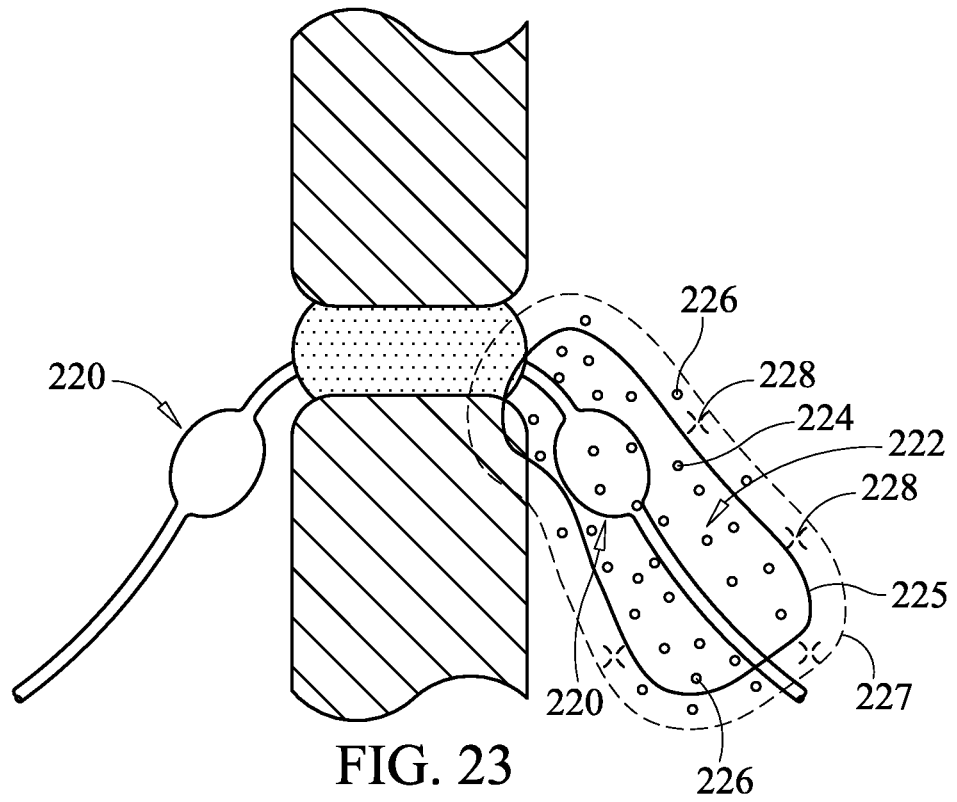
FIG. 23 illustrates delivery of a therapeutic agent to soft tissue surrounding a spinal canal utilizing a gel with dispersed microspheres.

Alternatively, rather than directly admixing the therapeutic agent into the gel, the present invention also contemplates instead dispersing microspheres within the gel, the microspheres loaded with the therapeutic agent. In one embodiment, the microspheres provide for a sustained release of the therapeutic agent. In yet another embodiment, the gel, which is biodegradable, prevents the microspheres from releasing the therapeutic agent; the microspheres thus do not release the therapeutic agent until they have been released from the gel. This embodiment is depicted in FIG. 23, which shows a gel 222 deployed around a nerve root 220, the targeted tissue site. Dispersed within the gel 222 are a plurality of microspheres 226 that encapsulate the desired therapeutic agent. Dashed line 227 indicates the original deployment region of the gel 222; solid line 225 indicates the current deployment region of the gel 222 due to degradation of the gel 222. Microspheres 226 are thus released from the gel 222. Certain of these microspheres 228 degrade once released from the gel 222, thus releasing the therapeutic agent.

It will be appreciated that a localized delivery device, such as a pump or the like, may be used to deliver the microspheres to the targeted tissue site. Similarly, a pump may be used to deliver the present invention gel, either with or without microspheres, to the target site. Examples of localized delivery systems are presented in co-pending U.S. patent application Ser. No. 11/091,348, which is incorporated herein by reference.

The use of depot implants to deliver anti-inflammatory or anabolic compounds to intervertebral discs or articulating joints has not been previously disclosed. The specific designs disclosed and contemplated in this invention provide a way to insert depot implants into discs or joint capsules with minimal tissue disruption and interfering with normal joint motion. It also prevents the depots from migrating away from the inflamed tissue and allowing for more uniform distribution of the drug.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A method for delivering a therapeutic agent to a targeted tissue site, the method comprising injecting into the targeted tissue site a drug depot comprising a body having opposite sides and at least two angled flexible barbs extending from the opposite sides of the body, wherein the drug depot comprises a plurality of microspheres encapsulating the therapeutic agent, and the drug depot is configured to release the microspheres in the targeted tissue site.

2. The method of claim 1 wherein the targeted tissue site is the annulus fibrosus.

3. The method of claim 1 wherein the targeted tissue site is the nucleus pulposus.

4. The method of claim 1 wherein the therapeutic agent is an anti-inflammatory agent.

5. The method of claim 4 wherein the anti-inflammatory agent is specific for a target selected from the group consisting of TNF, IL-1, IL-6, IL-8, IL-12, IL-15, IL-17, IL-18, GM-CSF, M-CSF, MCP-1, MIP-1, RANTES, ENA-78, OSM, FGF, PDGF, and VEGF.

6. The method of claim 1 wherein the therapeutic agent is an osteoinductive growth factor.

7. The method of claim 6 wherein the osteoinductive growth factor is selected from the group consisting of BMP-1, BMP-2, rhBMP-2, BMP-3, BMP-4, rhBMP-4, BMP-5, BMP-6, rhBMP-6, BMP-7 (0P-1), rhBMP-7, BMP-8, BMP-9, BMP-10, BMP-11, BMP-12, BMP-13, BMP-14, BMP-15, BMP-16, BMP-17, BMP-18, GDF-5, LIM mineralization protein, platelet derived growth factor (PDGF), transforming growth factor f3 (TGF-f3), insulin-related growth factor-I (IGF-I), insulin-related growth factor-II (IGF-II), fibroblast growth factor (FGF), beta-2-microglobulin (BDGF II), and rhGDF-5.

8. The method of claim 1 wherein the therapeutic agent is a kinase inhibitor.

9. The method of claim 8 wherein the kinase inhibitor is selected from the group consisting of Gleevec, Herceptin, Iressa, imatinib (STI571), herbimycin A, tyrphostin 47, erbstatin, genistein, staurosporine, PD98059, SB203580, CNI-1493, VX-50/702, SB203580, BIRB 796, Glaxo P38 MAP Kinase inhibitor, RWJ67657, U0126, Gd, SC10-469, RO3201195, and Semipimod.

10. The method of claim 1 wherein the therapeutic agent is ISIS2302 or GI 129471.

11. The method of claim 1 wherein the plurality of microspheres have a particle size range of from about 8 µm to about 15 µm.

12. The method of claim 11 wherein the plurality of microspheres are lipid containing microspheres.

13. The method of claim 1, wherein the plurality of microspheres have a particle size range of from about 5 µm to about 30 µm.

14. The method of claim 1, wherein the at least two angled flexible barbs are part of an anchoring system which provides a surface adapted to abut against a tissue.

15. The method of claim 14, wherein the anchoring system further comprises an end cap disposed on an end of the body of the drug depot.

16. The method of claim 1, wherein the at least two angled flexible barbs also comprise a plurality of microspheres.

17. The method of claim 1, wherein each of the at least two angled flexible barbs comprises a point adapted to allow forward translational movement of the body and limit backward translational movement of the body from the targeted tissue.

18. The method of claim 1, wherein the at least two angled flexible barbs are configured to release the microspheres into the targeted tissue site.

* * * * *